(12) United States Patent
Sasaki et al.

(10) Patent No.: US 10,071,144 B2
(45) Date of Patent: *Sep. 11, 2018

(54) CELL THERAPY FOR THE TREATMENT OF NEURODEGENERATION

(71) Applicant: NC MEDICAL RESEARCH INC., Minato-ku, Tokyo (JP)

(72) Inventors: Keishin Sasaki, Meguro-ku (JP); Thomas N. Chase, Washington, DC (US); Minako Koga, Rockville, MD (US)

(73) Assignee: NC MEDICAL RESEARCH INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/819,639

(22) PCT Filed: Feb. 6, 2013

(86) PCT No.: PCT/US2013/024826
§ 371 (c)(1),
(2) Date: May 20, 2013

(87) PCT Pub. No.: WO2014/123516
PCT Pub. Date: Aug. 14, 2014

(65) Prior Publication Data
US 2014/0219969 A1    Aug. 7, 2014

(51) Int. Cl.
*C12N 5/077* (2010.01)
*A61K 38/49* (2006.01)
*C12N 5/078* (2010.01)
*A61K 38/48* (2006.01)
*A61K 35/28* (2015.01)

(52) U.S. Cl.
CPC .......... *A61K 38/49* (2013.01); *A61K 38/4886* (2013.01); *C12N 5/0648* (2013.01); *A61K 35/28* (2013.01)

(58) Field of Classification Search
None
See application file for complete search history.

(56) References Cited

U.S. PATENT DOCUMENTS

| | | |
|---|---|---|
| 5,108,759 A | 4/1992 | Ranney |
| 5,633,283 A | 5/1997 | Kingston et al. |
| 5,733,542 A | 3/1998 | Haynesworth et al. |
| 5,811,094 A | 9/1998 | Caplan et al. |
| 7,807,458 B2 * | 10/2010 | Schiller et al. ............... 435/325 |
| 2003/0059414 A1 | 3/2003 | Ho et al. |
| 2004/0259254 A1 | 12/2004 | Honmou et al. |
| 2005/0169896 A1 | 8/2005 | Li et al. |
| 2006/0047743 A1 | 3/2006 | Yuan et al. |
| 2006/0062771 A1 | 3/2006 | Honmou et al. |
| 2006/0113731 A1 | 6/2006 | Stocchiero |
| 2006/0153799 A1 | 7/2006 | Zhao et al. |
| 2006/0172303 A1 | 8/2006 | Lehnert |
| 2006/0275272 A1 | 12/2006 | Li et al. |
| 2007/0128174 A1 | 6/2007 | Kleinsek et al. |
| 2007/0178591 A1 | 8/2007 | Honmou et al. |
| 2007/0298497 A1 * | 12/2007 | Antwiler ............... C12N 5/0663 435/401 |
| 2008/0138319 A1 * | 6/2008 | Deng et al. .................. 424/93.2 |
| 2009/0162327 A1 | 6/2009 | Li et al. |
| 2009/0191159 A1 | 7/2009 | Sakurada et al. |
| 2009/0317366 A1 | 12/2009 | Shen et al. |
| 2010/0254953 A1 | 10/2010 | Honmou et al. |
| 2011/0250183 A1 | 10/2011 | Picard et al. |
| 2011/0251629 A1 | 10/2011 | Galdonik et al. |
| 2011/0263022 A1 * | 10/2011 | Krause et al. ................ 435/401 |
| 2011/0268710 A1 | 11/2011 | Sanberg et al. |

FOREIGN PATENT DOCUMENTS

| | | |
|---|---|---|
| JP | 2008539745 | 11/2008 |
| JP | 2009183307 A | 8/2009 |
| JP | 2009540865 A | 11/2009 |
| WO | 99/043286 | 9/1999 |
| WO | 00/012683 | 3/2000 |
| WO | 00/31545 A1 | 6/2000 |
| WO | 00/069448 A1 | 11/2000 |
| WO | 03/038074 A1 | 5/2003 |
| WO | 03/038075 A1 | 5/2003 |
| WO | 03/038090 A1 | 5/2003 |
| WO | 2005/007176 A1 | 1/2005 |
| WO | 2006/120030 | 11/2006 |
| WO | 2009/034708 | 3/2009 |

OTHER PUBLICATIONS

Zhang et al., Bone marrow stromal cells protect oligodendrocytes from oxygen-glucose deprivation injury, 2008, Journal of neuroscience research 86(7): 1501-1510.*
Lee et al., Human neural stem cells over-expressing VEGF provide neuroprotection, angiogenesis and functional recovery in mouse stroke model, 2007, PloS one 2(1): e156.*
Bonab, Mandana M., et al. "Aging of mesenchymal stem cell in vitro." BMC cell biology 7.1 (2006): 14.*
Nardi, N. Beyer, and L. da Silva Meirelles. "Mesenchymal stem cells: isolation, in vitro expansion and characterization." Stem cells. Springer Berlin Heidelberg, 2008. 249-282.*

(Continued)

*Primary Examiner* — Robert J Yamasaki
(74) *Attorney, Agent, or Firm* — Sughrue Mion, PLLC

(57) ABSTRACT

Methods are described for the isolation and selection of a heterogeneous bone marrow cell population, called NCS-01, that is effective at treating neurodegeneration. For example, NCS-01 cells are shown to treat neurodegeneration caused by ischemia. In vivo studies demonstrate that selected NCS-01 cell populations treat neurodegeneration in a standard rat middle cerebral artery occlusion (MCAO) animal model under conditions of transient or permanent total arterial occlusion. These studies also disclose that when the neurodegeneration is caused by ischemic stroke, combining the administration of a selected NCS-01 cell population with thrombolytic agents and/or mechanical methods of clot removal leads to a decrease in the volume of infarction caused by acute onset neurodegeneration. The disclosed cell therapy promises to make a significant clinical impact on patient survival after stroke.

6 Claims, 11 Drawing Sheets

(56) References Cited

OTHER PUBLICATIONS

Joyce, Nanette, et al. "Mesenchymal stem cells for the treatment of neurodegenerative disease." Regenerative medicine 5.6 (2010): 933-946.*
Vogel, Wichard, et al. "Heterogeneity among human bone marrow-derived mesenchymal stem cells and neural progenitor cells." Haematologica 88.2 (2003): 126-133.*
Paolo Bianco et al., "Bone Marrow Stromal Stem Cells: Nature, Biology, and Potential Applications", Stem Cells, 2001, 19(3): 180-192.
Anthony W.S. Chan et al., "Generation of Transgenic Monkeys with Human Inherited Genetic Disease", Methods, 2009, 49(1): 78-84.
Geoffrey A. Donnan et al., "Stroke", Lancet, 2008, 371: 1612-1623.
Sharon M. Graham et al., "Animal Models of Ischemic Stroke: Balancing Experimental Aims and Animal Care", Comparative Medicine, 2004, 54(5): 486-496.
LL Håheim et al., "Risk factors of stroke incidence and mortality. A 12-year follow-up of the Oslo Study", Stroke, 1993, 24: 1484-1489.
Per Harmsen et al., "Long-Term Risk Factors for Stroke: Twenty-Eight Years of Follow-Up of 7457 Middle-Aged Men in Goteborg, Sweden", Stroke, 2006, 37: 1663-1667.
Brandon K. Harvey et al., "Transgenic animal models of neurodegeneration based on human genetic studies", J. Neural. Transm., 2011, 118(1): 27-45.
Donald Lloyd-Jones et al., "Heart Disease and Stroke Statistics—2009 Update: A Report From the American Heart Association Statistics Committee and Stroke Statistics Subcommittee", Circulation, 2009, 119: e21-e181.
Cristina Malagelada et al., "Histamine $H_2$-Receptor Antagonist Ranitidine Protects Against Neural Death Induced by Oxygen-Glucose Deprivation", Stroke, 2004, 35: 2396-2401.
Edward Rockenstein et al., "Transgenic animal models of neurodegenerative diseases and their application to treatment development", Advanced Drug Delivery Reviews, 2007, 59: 1093-1102.
Wayne Rosamond et al., "Heart Disease and Stroke Statistics—2007 Update: A Report From the American Heart Association Statistics Committee and Stroke Statistics Subcommittee", Circulation, 2007, 115: e69-e171.
Takao Yasuhara et al., "Notch-Induced Rat and Human Bone Marrow Stromal Cell Grafts Reduce Ischemic Cell Loss and Ameliorate Behavioral Deficits in Chronic Stroke Animals", Stem Cells and Development, 2009, 18: 1501-1513.
U.S. Appl. No. 60/134,344, filed May 14, 1999.
Akiyama et al., "Transplantation of Clonal Neural Precursor Cells Derived from Adult Human Brain Establishes Functional Peripheral Myelin in the Rat Spinal Cord," Experimental Neurology, 2001, pp. 27-39, vol. 167, Academic Press, Inc.
Archer et al., "Myelination by Cryopreserved Xenografts and Allografts in the Myelin-Deficient Rat,"Experimental Neurology, 1994, pp. 268-277, vol. 125, Academic Press, Inc.
Armstrong, R.J., et al., Survival, Neuronal Differentiation, and Fiber Outgrowth of Propagated Human Neural Precursor Grafts in an Animal Model of Huntington's Disease. Cell Transplant 2000; 9(1)55-64.
Azizi et al., "Engraftment and Migration of Human Bone Marrow Stromal Cells Implanted in the Brains of Albino Rats Similarities to Astrocyte Grafts," Proceedings of the National Academy of Science of USA, Medical Sciences, vol. 95, No. 7, 1998, pp. 3908-3913.
Barker, R.A., Prospects for the Treatment of Parkinson's Disease Using Neural Grafts, Expert Opinion on Pharmacotherapy. 2000 1(5):889-902.
Berkelaar et al, "Axotomy Results in Delayed Death and Apoptosis of Retinal Ganglion Cells in Adult Rats", J Neuroscience. 1994:14(7):4368-74).
Bianco et al., "Marrow stromal stem cells", Clinical Investigation., 2000, 105: 1663-1668.

Bjartmar, C. et al., "Axonal and neuronal degeneration in multiple sclerosis: mechanisms and functional consequences", Curr Opin Neurol. 2001; 14(3): 271-8. Abstract.
Bjorklund A et al. 2000. "Cell replacement therapies for central nervous system disorders". Nat Neuroscience vol. 3: No. 6 537-544.
Bjornson et al., "Turning Brain into Blood: A Hematopoietic Fate Adopted by Adult Neural Stem Cells in Vivo," Science, 1999, pp. 534-537, vol. 283.
Blakemore et al., "Extensive Oligodendrocyte Remyelination following Injection of Cultured CentralNervous System Cells into Demyelinating Lesions in Adult Central Nervous System," Dev. Neurosci., 1988 pp. 1-11, vol. 10, S. Karger AG, Basel.
Blakemore, "Remyelination of CNS axons by Schwann cells transplanted from the sciatic nerve," Nature, 1997, pp. 68-69, vol. 266.
Borlongan CV. "Transplantation therapy for Parkinson's disease". Exp. Opin. Invest Drugs (2000) 9: 2319-2330.
Borlongan, C.V., et al. "Cerebral Ischemia and CNS Transplantation: Differential Effects of Grafted Fetal Rat Striatal Cells and Human Neurons Derived From a Clonal Cell Line". Neuroreport. 1998 16;9(16): 3703-9.
Borlongan, C.V. et al., "Neural Transplantation for Neurodegenerative Disorders". Lancet 1999 353 (suppl 1): 29-30.
Campagnoli et al., "Identification of Mesenchymal Stem/Progenitor Cells in Human First-Trimester Fetal Blood, Liver and Bone Marrow", Blood, 2001, 2396-2402, 98, 8.
Chalmers-Redman et al., "In Vitro Propagation and Inducible Differentiation of Multipotential Progenitor Cells from Human Fetal Brain," Neuroscience, 1997, pp. 1121-1128, vol. 76, No. 4, IBRIO, Published by Elsevier Science Ltd, Great Britain.
Chen et al., "Intravenous bone marrow stromal cell therapy reduces apoptosis and promotes endogenous cell proliferation after stroke in female rat," J. Neurosci. Res., 2003, 73:778-786.
Chen J. et al., 2001, "Therapeutic Benefit of Intravenous Administration of Bone Marrow Stromal Cells After Cerebral Ischemia in Rats". Stroke 32: 1005-1011.
Chen J., et al., "Intracerebral transplantation of bone marrow with BDNF after MCAo in rat". Neuropharmacology 2000 39(5):711-6.
D'Allemand, G., "Laboratory Instrumentation", 4 Ed., Haven MC et al., ed., Wiley and Sons, 1995, pp. 31-34.
Deans et al., "Mesenchymal Stem Cells: Biology and Potential Clinical Uses", Experimental Hematology, International Society for Experimental Hematology, Elsevier, vol. 28, 2000, pp. 875-884.
Definitions of "neurology" and "disorder". Webster's College Dictionary (Random House, 1991). pp. 386-387, 909.
Devine et al., "Mesenchymal stem cells distribute to a wide range of tissues following systemic infusion into nonhuman primates," Blood, 2003, 101:2999-3001.
Devine SM et al. 2001. "Mesenchymal stem cells are capable of homing to the bone marrow of non-human primates following systemic infusion". Exp. Hematol. 29: 244-255.
Dinsmore, J. H., "Treatment of Neurodegenerative Diseases with Neural Cell Transplantation". Expert Opinion on Investigational Drugs. 1998 7(4): 527-34.
Eglitis et al., "Targeting of marrow-derived astrocytes to the ischemic brain", NeuroReport (1999), 10, pp. 1289-1292.
Eglitis, Martin A. et al, "Hematopoietic cells differentiate into both microglia and macroglia in the brains of adult mice", Proc. Natl. Acad. Sci. USA vol. 94, pp. 4080-4085, 1997.
Fink, J. S., et al., "Porcine Xenografts in Parkinson's Disease and Huntington's Disease Patients: Preliminary Results". Cell transplantation 2000 9(2)273-8.
Fisher, L. J., "Neural Precursor Cells: Applications for the Study and Repair of the Central Nervous System". Neurobiology Disease. 1997;4(1):1-22.
Flax et al., "Engraftable human neural stem cells respond to developmental cues, replace neurons, and express foreign genes," Nature Biotechnology, 1998, pp. 1033-1039, vol. 16.
Franklin et al., "Schwan Cell-Like Myelination Following Transplantation of an Olfactory Bulb-Ensheathing Cell Line Into Areas of Demyelination in the Adult CNS," GLIA, 1996, pp. 217-224, vol. 17,1996 Wiley-Liss, Inc.

(56) References Cited

OTHER PUBLICATIONS

Freeman, T. B., et al., "Transplanted Fetal Striatum in Huntington's Disease: Phenotypic Development and Lack of Pathology". Proc Natl Acad Sci .USA. 2000 5;97(25):13877-82.

Fricker-Gates, R.A., et. al.,"Neural Transplantation: Restoring Complex Circuitry in the Striatum". Restorative Neurology Neuroscience. 2001; 19(1-2):119-38.

Gage et al., "Survival and differentiation of adult neuronal progenitor cells transplanted to the adult brain," Proc. Natl. Acad. ScL USA, 1995, pp. 11879-11883, vol. 92.

Galy et al., "Hematopoietic Progenitor Cells of Lymphocytes and Dendritic Cells," Journal of Immunotherapy, Lippincott-Raven Publishers, vol. 21, No. 2, 1998, pp. 132-141.

Gao et al., "The dynamic in vivo distribution of bone marrow-derived mesenchymal stem cells after infusion", Cells Tissues Organs, 2001, 169:12-20.

Gessani et al., "Macrophages", Paulnock DM, ed., Oxford University Press, 2000, p. 45-50.

Gumpel, "Transplantation of Human Embryonic Oligodendrocytes into Shiverer Brain," Annals New York Academy of Sciences, 1987, pp. 71-85, vol. 495.

Halfpenny, C. et al. "Cell Transplantation, Myelin Repair, and Multiple Sclerosis". 2002, Lancet Neurol 1:31-40.

Haynesworth et al., "Cell Surface Antigens on Human Marrow-Derived Mesenchymal Cells are Detected by Monoclonal Antibodies", Bone, 1992, 13(1):69-80.

Helmuth, "Stem Cells Her Call of Injured Tissue". Neuroscience. Science. 2000 24; 290(5496): 1479-810).

Honmou et al., "Restoration of Normal Conduction Properties in Demyelinated Spinal Cord Axons in the Adult Rat by Transplantation of Exogenous Schwann Cells," The Journal of Neuroscience, 1996, pp. 3199-3208, vol. 16, No. 10, 1996 Society for Neuroscience.

Imaizumi et al., "Transplanted Olfactory Ensheathing Cells Remyelinate and Enhance Axonal Conduction in the Demyelinated Dorsal Columns of the Rat Spinal Cord," The Journal of Neuroscience, 1998, pos. 6176-6185, vol. 18, No. 16, 1996 Society for Neuroscience.

Javazon et al., "Rat Marrow Stromal Cells are More Sensitive to Plating Density and Expand More Rapidly from Single-Cell-Derived Colonies than Human Marrow Stromal Cells", Stem Cells, 2001, 219-225, 19.

Kato et al., "Transplantation of Human Olfactory Ensheathing Cells Elicits Remyelination of Demyelinated Rat Spinal Cord," GLIA, 2000, pp. 209-218, vol. 30, 2000 Wiley-Liss, Inc.

Koc et al., "Allogenic mesenchymal stem cell infusion for treatment of metachromatic leukodystrophy (MLD) and Hurler syndrome (MPS-IH)," Bone Marrow Transplant, 2002, 30(4):215-22.

Kopen et al., "Marrow stromal cells migrate throughout forebrain and cerebellum, and they differentiate into astrocytes after injection into neonatal mouse brains", Proc. Natl. Acad. Sc!. USA, 1999, pp. 10711-10716, vol. 96.

Kordower, J. H., et al. "Grafts of EGF Responsive Neural Stem Cells Derives From GFAP-Hngf Transgenic Mice: Trophic and Tropic Effects in a Rodent Model of Huntington's Disease", Journal of Comparative Neurology. 1997; 387:96-113.

Kornek, et al, "Multiple Sclerosis and Chronic Autoimmune Encephalomyelitis: A Comparative Quantitative Study of Axonal Injury in Active, Inactive, and Remyelinated Lesions", American Journal Pathology 2000, 157: 267-276.

Lane et al., "Stromal-Derived Factor 1-Induced Megakaryocyte Migration and Platelet Production is Dependent on Matrix Metalloproteinases", Blood, vol. 96, No. 13, pp. 4152-4159, 2000.

Lassmann, H.. "Stem Cell and Progenitor Cell Transplantation in Multiple Sclerosis: The Discrepancy Between Neurobiological Attraction and Clinical Feasibility". 2005, J. Neurol Sci 233: 83-86.

Li Y, et al. "Intrastriatal Transplantation of Bone Marrow Nonhematopoietic Cells Improves Functional Recovery After Stroke in Adult Mice". J Cereb Blood Flow Metab 2000 ;20(9):1311-9.

Li, Y, et al. "Adult Bone Marrow Transplantation After Stroke in Adult Rats. Cell transplant". 2001 10(1): 31-40.

Liu, X.Z. et al., "Neuronal and Glial Apoptosis After Traumatic Spinal Cord Injury". Journal of Neuroscience 1997; 17:5395-406.

Lois et al., "Proliferating subventricular zone cells in the adult mammalian forebrain can differentiate into neurons and glia", Proc. Natl. Acad. Sci. USA, 1993, pp. 2074-2077, vol. 90.

Lu, Dunyue, et al, "Adult bone marrow stromal cells administered intravenously to rats after traumatic brain injury migrate into brain and improve neurological outcome", Regeneration and Transplantation, vol. 12, No. 3, 2001, pp. 559-563.

Macleod MA. "Potential treatments and treatment strategies in Creutzfeldt-Jakob disease". 2003, I Drugs 6:345-50. Abstract only.

Majumdar et al., "Phenotypic and Functional Comparison of Cultures of Marrow-Derived Mesenchymal Stem Cells (MSCs) and Stromal Cells," J. Cell. Physiol., 1998, 176(1):57-66.

Martin, L. J., "Neuronal cell death in nervous system development, disease, and injury International journal of molecular medicine", (2001) 7 (5) p. 455-78.

Mattson MP. 2000. "Emerging neuroprotective strategies for Alzheimer's disease: dietary restriction, telomerase activation, and stem cell therapy". Exp Gerontol 35: 489-502.

Mattson, M. P., "Apoptosis in Neurodegenerative Disorders". Nature Reviews Molecular Cell Biology 1, 120-130 (2000).

McCARTHY, D.A., "Cytometric Analysis of Cell Phenotype and Function", Cambridge University Press, 2001, pp. 20-24 and 222-224.

McDonald, J. W., et al., "Transplanted embryonic stem cells survive, differentiate and promote recovery in injured rat spinal cord". Nature Medicine. 1999 5(12):1410-2.

Mezey E., et al. "Bone marrow: a possible alternative source of cells in the adult nervous system". 2000 29;405(1-3):297-302.

Morshead et al., "Neural Stem Cells in the Adult Mammalian Forebrain: A relatively Quiescent Subpopulation of Subependymal Cells," Neuron, 1994, pp. 1071-1082, vol. 13, 1994, Cell Press.

Moyer et al., "Culture, Expansion, and Transplantation of Human Fetal Neural Progenitor Cells", Transplantation Proceedings, 1997, pp. 1040-1041, vol. 29, 1997 Elsevier Science Inc.

Naegele, Janice R., et al., "Recent advancements in stem cell and gene therapies for neurological disorders and intractable epilepsy," Neuropharmacology, vol. 58, pp. 855-864, 2010.

Noti et al., "Structural and functional Characterization of the Leukocyte Integrin CD//d," The Journal of Biological Chemistry, The American Society for Biochemistry and Molecular Biology, Inc., vol. 270, No. 12, pp. 8859-8969, 2000.

Oostendorp et al., "Vla-4-Mediated Interactions Between Normal Human Hematopoietic Progenitors and Stromal Cells", Leukemia and Lymphoma, Harwood Academic Publishers, vol. 24, pp. 423-435, 1997.

Ourednik V., et al. "Neural stem cells are uniquely suited for cell replacement and gene therapy in the CNS". Novartis Foundation Symposium. 2000 231:242-62.

Patel et al., "Cell Separation: A Practical Approach", 1998, Oxford University Press, pp. 71-73.

Perlow, M. J., "Brain Grafting as a Treatment for Parkinson's Disease. Neurosurgery". 1987 20(2):335-42.

Peterson, et al, "Transected neuritis, apoptotic neurons, and reduced inflammation in cortical multiple sclerosis lesions", Annals of Neurology, 2001; 50: 389-400.

Peterson L. K, et al., "Inflammation, demyelination, neurodegeneration and neuroprotection in the pathogenesis of multiple sclerosis" Journal of Neuroimmunolgy, 184 (2007): pp. 37-44.

Pittenger, Mark F. et al., "Multilineage Potential of Adult Human Mesenchymal Stem Cells", Science, vol. 284, (1999), p. 143-147.

Plews, M et al., "Factors Affecting the Accuracy of Urine-Based Biomarkers of BSE". 2011, Proteome Sci 9(1): 6. 11 pages.

Quesenberry et al., "Strome! Cell Regulation of Lymphoid and Myeloid Differentiation," Blood Cells, Springer-Verlag, vol. 13, pp. 137-146, 1987.

Reynolds et al., "Generation of Neurons and Astrocytes from Isolated Cells of the Adult Mammalian Central Nervous System," Science, 1992, pp. 1707-1710, vol. 255.

Rice CM et al." Autologous bone marrow stem cells—properties and advantages", 2008, J Neurol Sci 265: 59-62.

(56) References Cited

OTHER PUBLICATIONS

Rothwell et al., "The Role of Interleukin 1 in Acute Neurodegeneration and Stroke: Pathophysiological and Therapeutic Implications", J. Clin. Invest. vol. 100, No. 11, 1997, 2648-2652.
Sasaki et al., "Transplantation of an Acutely Isolated Bone Marrow Fraction Repairs Demyelinated Adult Rat Spinal Cord Axons," GLIA, vol. 35, pp. 26-34 (2001).
Shetty, Ashor K., et al., "Concise Review: Prospects of Stem Cell Therapy for Temporal Lobe Epilepsy," Stem Cells, vol. 25, pp. 2396-2407, 2007.
Shihabuddin, L. S., et al. "The search for neural progenitor cells: prospects for the therapy of neurodegenerative disease". Mol Med Today. 1999 5(11): 474-80.
Studer, L., et al. Transplantation of Expanded Mesencephalic Precursors Leads to Recovery in Parkinsonian Rats. Nature Neuroscience 1998 1(14):290-5.
Svendsen et al., "Long-Term Survival of Human Central Nervous System Progenitor Cells Transplanted into a Rat Model of Parkinson's Disease," Experimental Neurology, 1997, pp. 135-146, vol. 148, 1997 Academic Press.
Szilvassy et al., "Differential Homing and Engraftment Properties of Hematopoietic Progenitor Cells From Murine Bone Marrow, Mobilized Peripheral Blood and Fetal Liver", Blood, 2001 vol. 98, No. 7, pp. 2108-2115.
Takeno et al., "Degeneration of spiral ganglion cells in the chinchilla after inner hair cell loss induced by carboplatin", Audiology and Neuro-Otology, 1998 vol. 3, pp. 281-290.
Thalmeier, Karin, et al., "Mesenchymal Differentiation and Organ Distribution of Established Human Stromal Cell Lines in NOD/SCID Mice", Acta Haematol 2001; 105:159-165.
The BCCA Cancer Drug Manual: entry for thiotepa; http://www.bccancer.bc.ca/NR/rdonlyres/4AC0469B-EC23-4D2F-8401-4706E059DC55/30570/Thiotepamonograph_1ju105_RW.pdf.
Thomas et al., "Taber's Encyclopedic Medical Dictionary", F. A. Davis Co., 1997, pp. 257, 1168 and 1805.
Trapp et al.,"Neurodegeneration in Multiple Sclerosis: Relationship to Neurological Disability", Neuroscientist (1999) vol. 5, No. 1, pp. 48-57.
Turski et al., "A phosphonate quinoxalinedione AMPA antagonist for neuroprotection in stroke and trauma", Proc. Natl. Acad. Sci. USA vol. 95, pp. 10960-10965, 1998.
Ugozzoli et al, "Detection of specific alleles by using allele-specific primer extension followed by capture on solid support", GATA, vol. 9(4), pp. 107-112, 1992.
Utzschneider et al., "Transplantation of glial cells enhances action potential conduction of amyelinated spinal cord axons in the myelin-deficient rat," proc. Natl. Acad. Sci. USA, 1994, pp. 53-57, vol. 91.
Veizovic, Tina et al., "Resolution of Stroke Deficits Following Contralateral Grafts of Conditionally Immortal Neuroepithelial Stem Cells. Stroke". 2001;32:1012-1019.
Verloes A. et al, "Genetic and clinical aspects of lissencephaly", Rev Neurol (Paris), 2007, 163:533-47. Abstract Only.
Vogel, G. "Capturing the Promise of Youth", Science, (1999) 286 (5448): 2238. 4 pages.
Wada R., et al., "Microglial activation precedes acute neurodegeneration in Sandhoff disease and is suppressed by bone marrow transplantation". Proc Natl Acad Sci USA. 2000 97(20):10954-9.
Wang, Jih-Shivan, et al., "The coronary delivery of marrow stromal cells for myocardial regeneration: Pathophysiologic and therapeutic implications", The Journal of Thoracic and Cardiovascular Surgery, vol. 122, No. 4, 2001, pp. 699-705.
Watt et al., "CD164—A Novel Sialomucin on CD34 Cells," Leukemia and Lymphoma, Harwood Academic Publishers, vol. 37, Nos. 1-2, pp. 1-25, 2000.

Woodbury et al., "Adult Rat and Human Bone Marrow Stromal Cells Differentiate Into Neurons," Journal of Neuroscience Research, vol. 61, pp. 364-370 (2000).
Yandava, B. D., et al. "Global" cell replacement is feasible via neural stem cell transplantation: evidence from the dysmyelinated shiverer mouse brain. Proc Natl Acad Sci USA. 1999 8;96(12):7029-34.
Yang J et al. "Cellular Remyelinating Therapy in Multiple Sclerosis". 2009, J Neurol Sci 276: 1-5.
Yin et al, Myelin-Associated Glycoprotein is a Myelin Signal That Modulates the Caliber of Myelinated Axons, J. Neurosci. 1998; 18: 1953-1962.
Yin et al., "AC133, A Novel Marker for Human Hematopoietic Stem and Progenitor Cells," Blood, vol. 90,No. 12, 1997, pp. 5002-5012.
Yuan, J., et al, "Apoptosis in the Nervous System", Nature (2000) 407, 802-9.
Brandes, A. A., et al., "Changing boundaries in the treatment of malignant gliomas," Expert Rev Anticancer Ther., 2001, pp. 357-370, vol. 1.
Greenberg, Harry S., et al., "Adult medulloblastoma: Multiagent chemotherapy", Neuro-Oncology, 2001, pp. 29-34, vol. 3.
Groothuis, Dennis R., "The blood-brain and blood-tumor barriers: A review of strategies for increasing drug delivery", Neuro-Oncology, 2000, pp. 45-59, vol. 2.
Ehtesham, Moneeb, et al., "The Use of Interleukin 12-secreting Neural Stem Cells for the Treatment of Intracranial Glioma," Cancer Research, 2002, pp. 5657-5663, vol. 62.
Bexell, Daniel, et al., "Toward Brain Tumor Gene Therapy Using Multipotent Mesenchymal Stromal Cell Vectors", Molecular Therapy, 2010, pp. 1067-1075, vol. 18, No. 6.
Sugita, Y., et al., "Acute focal demyelinating disease simulating brain tumors: histopathologic guidelines for an accurate diagnosis", Neuropathology, 2001, pp. 25-31, vol. 21(1).
Trancikova A. et al., "Genetic Mouse Models of Neurodegenerative Diseases", Progress in Molecular Boilogy and Translational Science, 100:419-482 (2011).
Search Report issued in corresponding International Patent Application No. PCT/US2013/24826 dated Jul. 12, 2013.
Singh et al., "Oxygen Glucose Deprivation Model of Cerebral Stroke in PC-12 Cells: Glucose as a limiting Factor", Toxicology Mechanisms and Methods, 19(2):154-160 (2009).
Iafrati et al., "Early results and lessong learned from a multicenter, randomized, double-blind trail of bone marrow aspirate concentrate in critical limb ischemia", J. of Vascular Surgery, 54(6):1650-1658 (2011).
Mauricio et al., "Intra-ARterial Infusion of Autologous Bond Marrow Mononuclear cells in patients with moderate to server middle cebral artery acute ischemic stroke", Cell Transplantation, 21(1):S13-S21 (2012).
Posel et al., "Density Gradient Centrifugation Comprises Bone Marrow Mononuclear Cell Yield", PLOS One, 7(12):e50293 (2012).
Communication for European Application No. 13874359.6 dated Sep. 9, 2016 (with Supplementary European Search Report).
Uchiyama et al., "Thrombolytics revisited-thrombolytic therapy in acute ischemic stroke", Igaku no ayumi, a separate volume, Blood Disorders, state of arts Ver. 3, Sep. 15, 2009, pp. 605-609. (12 pages total).
Nakazawa et al., "Current evolution of neuroendovascular intervention", Igaku no ayumi, a separate volume, Stroke, The vanguard of basic research and clinical medicine, Jun. 1, 2006, pp. 131-136. (11 pages total).
Sakai et al., Igaku no ayumi, vol. 191, No. 5, Nov. 6, 1999, pp. 744-749. (8 pages total).

* cited by examiner

CELL THERAPY FOR THE TREATMENT OF NEURODEGENERATION

CROSS REFERENCE TO RELATED APPLICATIONS

This application is a National Stage of International Application No. PCT/US2013/024826 filed Feb. 6, 2013, the contents of all of which are incorporated herein by reference in their entirety.

FIELD OF THE INVENTION

The disclosure describes cell compositions and methods for the treatment of neurodegeneration.

BACKGROUND

Neurodegeneration is a pathological state that results in neural cell death. Although the causes of neurodegeneration may be diverse and not always ascertainable, a large number of neurological disorders share neurodegeneration as a common pathological state. For example, Alzheimer's disease, Parkinson's disease, Huntington's disease, and amyotrophic lateral sclerosis (ALS) all cause chronic neurodegeneration, which is characterized by a slow, progressive neural cell death over a period of several years, whereas acute neurodegeneration is characterized by a sudden onset of neural cell death as a result of ischemia, such as stroke, or trauma, such as traumatic brain injury, or as a result of axonal transection by demyelination or trauma caused, for example, by spinal cord injury or multiple sclerosis.

Neurodegeneration can also be triggered by a wide variety of neural cell insults resulting from, for example, alcohol abuse, drug addiction, exposure to neurotoxins and radiation. Evidence for neurodegeneration can even be found in dementia, epilepsy, various psychiatric disorders and as part of the normal aging process.

Regardless of the underlying cause, a growing body of evidence indicates that, once neurodegeneration is triggered, the outcome for all these disorders is invariably the same—the ultimate death of neural cells.

Stroke involves acute neurodegeneration (the rapid loss of central nervous system neural cells with attending loss of function) due to occlusion (ischemic stroke) or rupture (hemorrhage) of a blood vessel leading to or within the brain. It usually constitutes a medical emergency, since it can cause permanent neurological damage, systemic complications, and even death. Stroke is the leading cause of adult disability in the United States and Europe and it is the number two cause of death worldwide. Stroke accounts for more than one in every fifteen deaths in the U.S. and ranks third amongst all causes of death, behind heart disease and cancer (American Heart Association. Heart Disease and Stroke Statistics—2009 Update. Dallas, Tex.: American Heart Association; 2009; Rosamond et al. Heart disease and stroke statistics—2007 update: a report from the American Heart Association Statistics Committee and Stroke Statistics Subcommittee. Circulation. 2007; 115: e69-e171). Every third stroke has a fatal outcome (Häheim et al. Risk factors of stroke incidence and mortality. A 12-year follow-up of the Oslo Study. *Stroke.* 1993; 24(10):1484-9). About 6% of all deaths before age 65 and 10% of all deaths thereafter, are due to stroke (Donnan et al. Stroke. *Lancet.* 2008; 371 (9624):1612-23). The statistical data therefore demonstrate that severe disability is an unfortunate, but all too frequent, outcome for many stroke victims. Indeed, stroke is the number one cause of inpatient Medicare reimbursement for long-term adult care. Total costs associated with the treatment and rehabilitation from stroke now exceed $45 billion per year and will undoubtedly continue to contribute to the overall increase in the cost of healthcare in the US as well as the other major industrialized nations.

Ischemic strokes are the most common form of stroke, accounting for over 80 percent of all strokes. They result from arterial blockage, usually due to thrombosis or less commonly due to embolism. Onset is generally abrupt and focal neurologic deficits typically ensue. About 20% of patients die within a few days, especially if the infarct is large. Another 10% of patients die within weeks of the initial stroke. Unfortunately, those who survive are usually severely disabled. Symptoms, depending on the area of the brain affected, include unilateral facial or limb weakness and sensory disturbances as well as cognitive and speech impairment. The larger the area of brain affected, the more functions are likely to be impaired. Some functional improvement may begin to occur within days and further recovery over several months is common. Nevertheless, the extent of recovery is unpredictable and generally incomplete. According to the American Stroke Association, of those who survive a stroke, 15 to 30% are permanently disabled, and 20% require institutional care three months after onset (Harmsen et al. Long-term risk factors for stroke: twenty-eight years of follow-up of 7457 middle-aged men in Göteborg, Sweden. Stroke. 2006; 37(7):1663-7).

Ischemic stroke leads to a core lesion, in which nerve cells die within minutes of oxygen deprivation, and a surrounding penumbra, a region that receives some blood-flow and therefore some oxygen, but less than normal. Cell death proceeds more slowly in the ischemic penumbra, typically over several hours, and is caused by variable anoxia and by toxic substances generated by the ischemic cascade and the release of glutamate in the core lesion. Current therapeutic interventions thus mainly target the alleviation of the injurious conditions in the stroke penumbra.

Treatments for acute ischemic stroke remain however limited.

Since brain damage occurs as a result of a reduction in blood flow to the brain, current therapies aim to remove the arterial blockage by either dissolving the clot (thrombolysis) or by removing the clot mechanically (thrombectomy). The faster blood flow is restored, the fewer brain cells die and the greater the chance that permanent sequelae can be averted.

At present, only two treatments are FDA approved for stroke in the United States:

Recombinant tissue plasminogen activator (rt-PA; Genentech), a drug that dissolves the arterial clot; and The Merci Retrieval System (Concentric Medical Inc.) and Penumbra System (Penumbra Inc.), a device that mechanically removes blood clots.

All the above therapeutic approaches have major limitations.

To be effective, therapy with thrombolytic agents must be performed within 3 to 4.5 hours of symptom onset which means only about 3% of patients with acute ischemic stroke receive effective rt-PA therapy. In addition, thrombolytic therapies carry a substantially increased risk of cerebral hemorrhage, which further limits their use in some individuals.

For the foregoing reasons, there is an unmet, urgent need in the art for safe and effective therapies that mitigate and/or prevent neurodegeneration, and especially neurodegeneration caused by ischemia.

SUMMARY OF THE INVENTION

Accordingly, in one embodiment, the present invention provides a heterogeneous subpopulation of bone marrow (BM) cells prepared by a process comprising:
a) obtaining a population of bone marrow cells from unprocessed bone marrow;
b) seeding the population of bone marrow cells at a low density on a plastic surface;
c) washing the seeded cell population to remove non-adherent cells;
d) culturing the adherent cell population to near confluence in serum-containing media;
e) serially passaging the population of cultured cells for no more than about 7 serial passages, wherein, at each passage, the cultured cells are seeded at a low density;
f) obtaining the heterogeneous subpopulation of bone marrow cells, wherein an effective amount of the heterogeneous subpopulation of bone marrow cells is effective at treating neurodegeneration.

In one aspect, an effective amount of the heterogeneous subpopulation of bone marrow cells is effective at treating neurodegeneration caused by ischemia.

In one aspect, the heterogeneous subpopulation of bone marrow cells is cultured in serum containing media.

In one aspect, the population of bone marrow cells are seeded at a density of about $10^2$-$10^6$ cells/cm$^2$.

In one aspect, the cultured cells are seeded at a density of about 750 cells/cm$^2$ or less in passaging.

The unprocessed bone marrow can be obtained from a subject who is not pre-treated with any agent that modulates cell division, for example, anti-neoplastic drugs used in chemotherapy including anti-metabolites, such as 5-fluorouracil.

In one aspect, the heterogeneous subpopulation of bone marrow cells cannot be isolated by density fractionation, e.g. a Ficoll™ or Percoll™ gradient, or by ACK (Ammonium-Chloride-Potassium) lysis.

In a further aspect of the invention, the heterogeneous subpopulation of bone marrow cells is further tested in an experimental model of neurodegeneration caused by ischemia, wherein only those cell populations that demonstrate the ability to treat neurodegeneration caused by ischemia are selected. The experimental model of neurodegeneration caused by ischemia can be an oxygen/glucose deprivation (OGD) cell culture model or a stroke animal model. In one aspect, the experimental model can be an oxygen/glucose deprivation (OGD) cell culture model followed by a stroke animal model.

In another aspect, after injection into the blood stream, cells within the heterogeneous subpopulation migrate to a site of neurodegeneration.

In one aspect, the neurodegeneration caused by ischemia is ischemic stroke.

In another embodiment, the invention also provides a method of treating neurodegeneration caused by ischemia, comprising injecting the heterogeneous subpopulation of bone marrow cells as described above into the blood stream of a mammal with neurodegeneration, wherein the injection of the heterogeneous subpopulation of bone marrow cells reduces a neurological deficit caused by the neurodegeneration.

When the neurodegeneration is caused by ischemic stroke, the method can further comprise an additional treatment to increase blood flow through an occluded blood vessel, wherein the injection of the heterogeneous subpopulation of bone marrow cells in combination with the additional treatment results in a greater reduction of the neurological deficit than after either additional treatment alone or injection of the heterogeneous subpopulation of bone marrow cells without the additional treatment.

In one aspect, the additional treatment to increase blood flow through an occluded blood vessel occurs at the same time as the injection of the heterogeneous subpopulation of bone marrow cells.

In another aspect, the additional treatment to increase blood flow through an occluded blood vessel occurs before the injection of the heterogeneous subpopulation of bone marrow cells.

When the neurodegeneration is caused by ischemic stroke, the blood vessel can be occluded by a blood clot. The blood clot can result from the rupture of an atherosclerotic plaque.

When the neurodegeneration is caused by ischemic stroke, the additional treatment to increase blood flow through an occluded blood vessel can include administering a thrombolytic agent. The thrombolytic agent can be at least one of streptokinase, urokinase and a recombinant tissue plasminogen activator. Further, the recombinant tissue plasminogen activator can be alteplase, reteplase, desmoteplase or tenecteplase.

In another aspect, when the neurodegeneration is caused by ischemic stroke, the additional treatment to increase blood flow through an occluded blood vessel may include mechanical removal of a blood clot from the occluded blood vessel.

In a further aspect, the blood clot can be captured with a filter.

In another aspect, when the neurodegeneration is caused by ischemic stroke, the additional treatment to increase blood flow through an occluded blood vessel may include performing an angioplasty and/or vascular stenting.

The heterogeneous subpopulation of bone marrow cells can be injected intravenously, intra-arterially, e.g. into the carotid artery, or intra-cerebrally.

In another embodiment, the invention also provides a method for treating neurodegeneration caused by ischemia, comprising injecting the heterogeneous subpopulation of bone marrow cells into the blood stream of a mammal with neurodegeneration caused by ischemia, wherein the injection of the heterogeneous subpopulation of bone marrow cells reduces the volume of an infarction caused by ischemia.

When the neurodegeneration is caused by ischemic stroke, the method can further comprise an additional treatment to increase blood flow through an occluded blood vessel, wherein the injection of the heterogeneous subpopulation of bone marrow cells in combination with the additional treatment results in a greater reduction of the volume of infarction than after either the additional treatment alone or injection of the heterogeneous subpopulation of bone marrow cells without the additional treatment.

In one aspect, when the neurodegeneration is caused by ischemic stroke, the additional treatment to increase blood flow through an occluded blood vessel comprises administering a thrombolytic agent. The thrombolytic agent can be at least one of streptokinase, urokinase and a recombinant tissue plasminogen activator. Further, the recombinant tissue plasminogen activator can be alteplase, reteplase, desmoteplase or tenecteplase.

In another aspect, when the neurodegeneration is caused by ischemic stroke, the additional treatment to increase blood flow through an occluded blood vessel can include performing an angioplasty and/or stenting.

In another aspect, when the neurodegeneration is caused by ischemic stroke, the additional treatment to increase blood flow through an occluded blood vessel can include mechanical removal of a blood clot near the site of the infarction.

According to a second method, the heterogeneous subpopulation of bone marrow cells can be injected intravenously, intra-arterially, e.g. into a carotid artery, or intra-cerebrally.

When the neurodegeneration is caused by ischemic stroke, the invention may also provide a kit comprising a thrombolytic agent and the heterogeneous subpopulation of bone marrow cells as described above. The thrombolytic agent can be at least one of streptokinase, urokinase and a recombinant tissue plasminogen activator. Further, the recombinant tissue plasminogen activator can be alteplase, reteplase or tenecteplase.

When the neurodegeneration is caused by ischemic stroke, the invention can further provide a kit comprising the heterogeneous subpopulation of bone marrow cells described above and a means for mechanical removal of a blood clot.

Additionally, when the neurodegeneration is caused by ischemic stroke, the invention can provide a composition for the treatment of neurodegeneration caused by ischemia comprising a thrombolytic agent, the heterogeneous subpopulation of bone marrow cells described above, and a carrier for injection of the composition. The thrombolytic agent can be at least one of streptokinase, urokinase and a recombinant tissue plasminogen activator. Further, the recombinant tissue plasminogen activator can be alteplase, reteplase or tenecteplase.

The invention can also provide a method of producing a heterogeneous subpopulation of bone marrow cells for the treatment of neurodegeneration, comprising:
  a) obtaining a heterogeneous population of bone marrow cells from unprocessed bone marrow;
  b) seeding the heterogeneous population of bone marrow cells at a low density onto a plastic surface,
  c) washing the seeded cell population to remove non-adherent cells;
  d) culturing the adherent cells from the washed population of cells to near confluence in serum containing media;
  e) serially passaging each of the population of cultured cells for no more than about seven serial passages, wherein, at each passage, the cultured cells are seeded at low density, thereby obtaining the heterogeneous subpopulation of bone marrow cells.

In one aspect, the unprocessed bone marrow described above can be obtained from a subject who is not pre-treated with any agent that modulates cell division, for example, anti-neoplastic drugs used in chemotherapy including antimetabolites, such as 5-fluorouracil.

In one aspect, the heterogeneous subpopulation of bone marrow cells cannot be isolated by density fractionation, e.g. a Ficoll™ or Percoll™ gradient, or by ACK (Ammonium-Chloride-Potassium) lysis.

In a further aspect of the invention, the heterogeneous subpopulation of bone marrow cells can be further tested in an experimental model of neurodegeneration caused by ischemia, wherein only those cell populations that demonstrate the ability to treat neurodegeneration caused by ischemia are selected. Experimental models of neurodegeneration caused by ischemia can be an oxygen/glucose deprivation (OGD) cell culture model and a stroke animal model. In one aspect, the experimental model can be an oxygen/glucose deprivation (OGD) cell culture model followed by a stroke animal model. In one aspect, both models can be used to test the heterogeneous subpopulation of bone marrow cells.

In another aspect, the present invention can also provide a method of optimizing an experimental protocol for the isolation of a heterogeneous cell population that treats neurodegeneration caused by ischemia, comprising the steps of:
  isolating a cell population according to an experimental protocol,
  wherein the cell population treats neurodegeneration caused by ischemia, and
  wherein the optimal parameters of each step of the protocol are determined by testing the effect each parameter has on the efficacy of the isolated cell population to treat neurodegeneration caused by ischemia in an experimental model of ischemia.

In one aspect, the parameters can include cell density at seeding, cell passage number, culture media composition or cell fractionation.

In another aspect, the experimental model of ischemia can be an oxygen/glucose deprivation (OGD) cell culture model or a stroke animal model, such as a middle cerebral artery occlusion (MCAO) animal model. Also both models can be used. In one aspect, the experimental model can be an oxygen/glucose deprivation (OGD) cell culture model followed by a stroke animal model.

The above-described aspects have many advantages, including the ability of the heterogeneous subpopulation of bone marrow cells to treat neurodegeneration caused by ischemic stroke. The cell population greatly diminishes the region of infarction and improves neurological function.

In combination with thrombolytic agents and mechanical methods of clot removal, the cell therapy promises to make a significant clinical impact on patient survival, functioning, and quality of life after stroke.

BRIEF DESCRIPTION OF THE DRAWINGS

The skilled artisan will understand that the drawings, described below, are for illustration purposes only. The figures are not intended to limit the scope of the teachings in any way.

FIG. 1 depicts the results from the screening of candidate bone marrow-derived cell sub-populations using the in vitro OGD model (FIGS. 1A, 1B and 1E) and the in vivo MCAO rat model (FIGS. 1C, 1D and 1F).

DETAILED DESCRIPTION

Figure 1A:
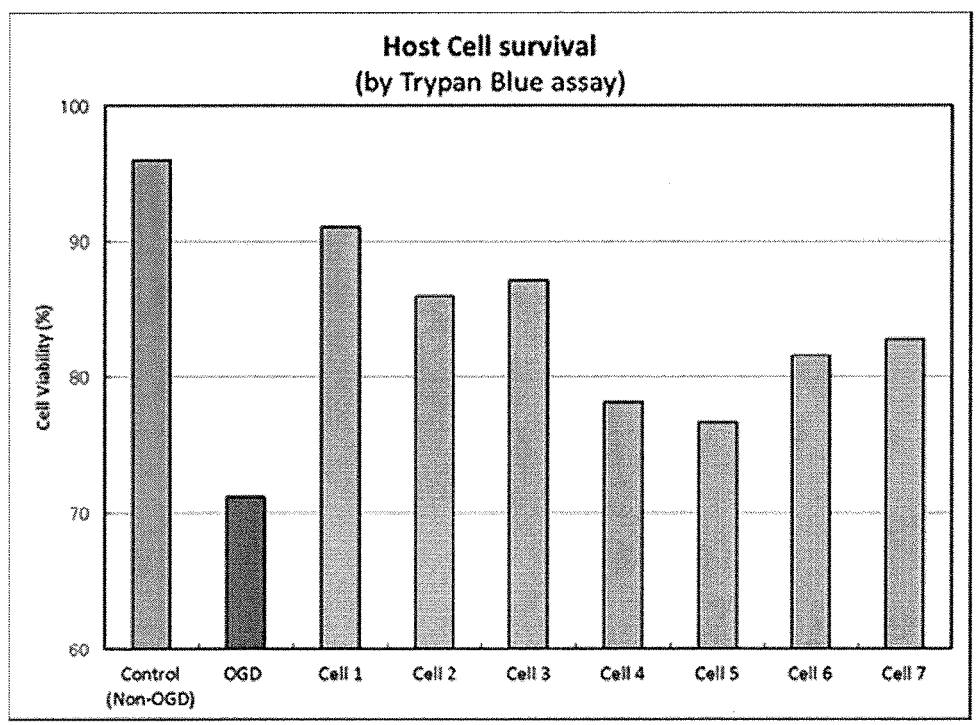
FIGS. 1A and 1B depict host cell survival and cytokine release (bFGF and IL-6) respectively in the in vitro OGD model in response to the presence or absence of 7 different candidate bone marrow-derived cell sub-populations.

The practice of the invention employs, unless otherwise indicated, conventional molecular biological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements; Sambrook, et al., Molecular Cloning: A Laboratory Manual, 2nd Edition, Cold Spring Harbor, N.Y. (1989).

Unless defined otherwise, all technical and scientific terms used herein have the same meaning as is commonly understood by one of skill in the art. The specification also provides definitions of terms to help interpret the disclosure and claims of this application. In the event a definition is not consistent with definitions elsewhere, the definition set forth in this application will control.

Bone marrow (BM) derived cells include a heterogeneous mixture of many different types of cells. Bone marrow is composed of two main cell systems that belong to two distinct lineages—the hematopoietic tissues and the associated supporting stroma. Thus, at least two distinct stem cells, namely hematopoietic stem cells (HSCs) and mesenchymal stem cells (MSCs), are known to co-exist in the bone marrow (Bianco, M. Riminucci, S. Gronthos, and P. G. Robey, "Bone marrow stromal stem cells: nature, biology, and potential applications," Stem Cells, vol. 19, no. 3, pp. 180-192, 2001).

MSCs can be broadly defined both by cell-surface markers and by their ability to adhere to tissue/cell culture plastic. Thus, MSC populations are necessarily heterogeneous, i.e. not a clonal cell population. Even if MSC sub-populations share one or more common cell surface markers, they can nevertheless differ significantly in their biological activity depending on the manufacturing method used to isolate them. This disclosure describes a two-step screening protocol for the identification of a heterogeneous bone marrow cell population that is effective at treating neurodegeneration including acute onset neurodegeneration caused by ischemia.

In a first step, bone marrow subpopulations are screened for their ability to attenuate the effect of oxygen glucose deprivation (OGD) in co-cultures comprising candidate bone marrow subpopulations and neural cells. The activity of candidate bone marrow subpopulations to attenuate neurodegeneration is assessed by measuring the secretion of trophic factors (bFGF and IL6) in the culture media as well as determining host cell survival in the OGD assay.

In a second step, bone marrow derived cell populations having the strongest activity in the OGD assay are then further screened by testing in an in vivo MCAO rat model of neurodegeneration caused by ischemia. This screening procedure facilitates the identification of a heterogeneous bone marrow subpopulation, called NCS-01, that greatly attenuates neurodegeneration caused by ischemia, as defined herein.

Unprocessed bone marrow cells are readily available to one of ordinary skill in the art.

As used herein, the term "unprocessed bone marrow" refers to a human bone marrow aspirate without any additional processing, such as density fractionation or cell sorting.

In other embodiments, "unprocessed bone marrow" is obtained from subjects that are not pre-treated with any agent that interferes with normal cell growth and division, including, for example, chemotherapy agents such as anti-mitotic or anti-metabolite agents.

Examples of such agents can be found in Cancer Principles and Practice of Oncology by V. T. Devita and S. Hellman (editors), 6th edition (Feb. 15, 2001), Lippincott Williams & Wilkins Publishers.

An "anti-metabolite" agent, as used herein, relates to a compound which inhibits or disrupts the synthesis of DNA resulting in cell death. Examples of an anti-metabolite include, but are not limited to, 6-mercaptopurine; cytarabine; fludarabine; flexuridine; 5-fluorouracil; capecitabine; raltitrexed; methotrexate; cladribine; gemcitabine; gemcitabine hydrochloride; thioguanine; hydroxyurea; DNA demethylating agents, such as 5-azacytidine and decitabine; edatrexate; and folic acid antagonists such as, but not limited to, pemetrexed.

As used herein, the term "density fractionation" refers to well-known laboratory procedures for the fractionation of bone marrow cells based on cell density using Ficoll-Paque™ or Percoll™ gradients. For example, Ficoll-Paque™ is placed at the bottom of a conical tube, and unprocessed bone marrow is then slowly layered on top of the Ficoll-Paque™. After centrifugation of the cells through the Ficoll gradient, the cells separate into layers according to density, from top to bottom: plasma and other constituents, a layer of mono-nuclear cells, called the buffy coat, comprising peripheral blood mononuclear cells (PBMCs) and mononuclear cells (MNCs) and erythrocytes and granulocytes in the pellet. This fractionation procedure separates erythrocytes from PBMCs. Ethylene diamine tetra-acetate (EDTA) and heparin are commonly used in conjunction with Ficoll-Paque™ to prevent clotting.

As used herein, the term "ACK lysis" refers to ammonium chloride potassium lysis buffer (ACK lysis buffer) for lysing of red blood cells in EDTA-anti-coagulated whole blood.

As used herein, the term "seeding the population of bone marrow cells at a low density" refers to the concentration of bone marrow cells added at the start of cell culture. In one aspect, the bone marrow cells are seeded at a density of about $10^2$ or about $10^3$ or about $10^4$ or about $10^5$ or about $10^6$ cells/cm². In a preferred aspect, the bone marrow cells are seeded at a density of about $10^5$ to about $10^6$ cells/cm².

As used herein, "neurodegeneration" refers to any pathological state that results in the progressive loss of structure or function of neural cells, including neural cell death. Thus, neurodegeneration is a pathological state caused by neurological disorders.

In one embodiment, the phrase "neural cell" includes both nerve cells (i.e., neurons, e.g., uni-, bi-, or multipolar neurons) and their precursors and glial cells (e.g., macroglia such as oligodendrocytes, Schwann cells, and astrocytes, or microglia) and their precursors.

In one embodiment, an "effective amount" refers to the optimal number of cells needed to elicit a clinically significant improvement in the symptoms and/or pathological state associated with neurodegeneration including slowing, stopping or reversing neurodegeneration, reducing a neurological deficit or improving a neurological response. In some embodiments, an effective amount of the NCS-01 cell population refers to the optimal number of cells needed to reduce the volume of infarction caused by the sudden onset of acute neurodegeneration after a stroke. An appropriate effective amount of the NCS-01 cell population for a particular organism may be determined by one of ordinary skill in the art using routine experimentation.

As used herein, "treating neurodegeneration" refers to the treatment of neurodegeneration by a NCS-01 cell population that results in a clinically significant improvement in the symptoms and/or pathological state associated with neurodegeneration including slowing, stopping or reversing neurodegeneration, reducing a neurological deficit or improving a neurological response.

As used herein, "thrombolytic agents" refers to drugs that are used in medicine to dissolve blood clots in a procedure termed thrombolysis. Non-limiting examples of thrombolytic drugs include tissue plasminogen tissue activator tPA, alteplase (Activase), reteplase (Retavase), tenecteplase (TNKase), anistreplase (Eminase), streptokinase (Kabikinase, Streptase) and urokinase (Abbokinase).

The following describes the procedures for isolating and characterizing a heterogeneous bone marrow cell sub population from whole, unprocessed bone marrow that is optimal for the treatment of neurodegeneration including the treatment of neurodegeneration caused by ischemia.

Isolation of Candidate Bone Marrow Cell Populations Effective for Treating Neurodegeneration Caused by Ischemia.

Whole, unprocessed bone marrow is harvested from a mammal that is not pre-treated with an anti-mitotic or anti-metabolite, such as 5-fluorouracil (5-FU).

The unprocessed bone marrow is then plated directly on to tissue/cell culture plastic and expanded by serial passaging in a serum containing media. At each passage, cells are seeded at very low cell density, i.e. approximately 750 cells/cm$^2$ or less, and cultured to near confluence before additional passaging. Non-adherent cells are removed by washing. As the bone marrow is not processed by density fractionation, the starting whole bone marrow cell population includes hematopoietic and non-hematopoietic cells as well as both nucleated and non-nucleated bone marrow cells.

Master (MCB) and Working Cell Banks (WCB) are then established preferably at passages 3 and 5, respectively and cryopreserved.

When needed, WCB cells are seeded at very low density, e.g. approximately 750 cells/cm$^2$ or less, and expanded in serum containing media before being harvested and cryopreserved using standard procedures.

A Two-Step Selection Protocol for Evaluating a Bone Marrow Cell Population's Ability to Attenuate Neurodegeneration 'Candidate' bone marrow cell populations can then be screened using a two-step procedure that selects the optimal bone marrow cell population for the treatment of neurodegeneration.

In the first step, candidate bone marrow cell populations are tested in an in vitro oxygen glucose deprivation assay where candidate bone marrow cell populations are co-cultured with neural cells under experimental conditions that mimic neurodegeneration. Cell populations that are shown to attenuate neurodegeneration in vitro are then screened for their ability to treat neurodegeneration in vivo.

In the second step, selected candidate bone marrow cell populations are evaluated in a rat MCAO model of neurodegeneration caused by ischemia. The candidate heterogeneous bone marrow cell population demonstrating the most activity to attenuate neurodegeneration in vivo is then selected.

The heterogeneous bone marrow cell population selected by this two-step screening procedure is called the NCS-01 cell population or NCS-01.

Identification of the Optimal Cell Culture Conditions for the Isolation of a Bone Marrow Cell Population with Neurodegeneration Attenuation Activity The two-step screening protocol is also useful in identifying the optimal experimental conditions such as cell density at seeding, cell passage number, culture media composition or cell fractionation for the culture of bone marrow cell populations that are able to treat neurodegeneration.

Thus, using the two screening procedure, the optimal reseeding cell concentration is about 750 cells/cm$^2$ or less at each passage. The optimal culture media is a serum containing media. NCS-01 cell populations can be passaged for no more than about 7, or about 6 or about 5 or about 4 or about 3 or about 2 passages from the initial plating of the whole, unprocessed bone marrow. Extended passaging i.e. beyond 7 passages from the initial plating of the whole, unprocessed bone marrow diminishes or abolishes NCS-01's ability to treat neurodegeneration in the OGD in vitro assay and in the MCAO rat model.

The OGD assay and the MCAO rat model of neurodegeneration are now described in detail below.

In Vitro Screening of Bone Marrow Cell Populations Capable of Treating Neurodegeneration Candidate bone marrow cell populations are first screened for their ability to prevent neurodegeneration in a neuron-astrocyte co-culture after culture conditions of oxygen-glucose deprivation (OGD) that simulate neurodegeneration caused by ischemia.

Primary mixed cultures of rat or human neurons and astrocytes are first exposed to oxygen glucose deprivation (OGD) culture conditions (for example, 8% oxygen, glucose free media) for about 0.5 to 3 hours to induce neurodegeneration. Oxygen glucose deprivation of the cell culture is then discontinued and the OGD induced neural cells are cultured under physiological conditions for 2 hours and then co-cultured in the presence of a candidate bone marrow cell population for an additional 3 hours. Neurodegeneration is then assessed by measuring host cell viability either in the presence or absence of the candidate bone marrow cell population at 0 and from 5 hours after OGD. Host cell (neurons and astrocytes) viability can be assessed using, for example, trypan blue staining and/or the MTT (3-(4,5-Dimethylthiazol-2-yl)-2,5-diphenyltetrazolium bromide) assay.

An increase in cell viability in the presence of a candidate bone marrow cell population as compared to the cell viability of a control (without the addition of the candidate bone marrow cell population) by about 5% or about 10% or about 15% or about 20% or about 25% or more indicates the candidate bone marrow cell population can protect and rescue neuron/astrocyte co-cultures from neurodegeneration caused by oxygen and glucose deprivation.

In addition, the culture media of neuron/astrocyte cell cultures subjected to OGD conditions in the presence or absence of candidate bone marrow cell populations can also be assayed for the induced secretion of trophic factors, for example, bFGF and/or IL-6 using commercially available ELISA kits.

In certain embodiments, candidate bone marrow cell populations are selected according to their ability to induce an increase in the amount of secreted bFGF and/or IL-6 in the media of neuron-astrocyte co-cultures in response to oxygen glucose deprivation, but not in the absence of oxygen glucose deprivation.

In other embodiments candidate bone marrow cell populations are selected according to their ability to induce an at least two-fold or greater increase in the amount of secreted bFGF and/or IL-6 in the media of neuron-astrocyte co-cultures in response to oxygen glucose deprivation, but not in the absence of oxygen glucose deprivation.

Candidate bone marrow cell populations that decrease the incidence of OGD-induced cell death and induce an increase in the amount of secreted trophic factors (such as bFGF and/or IL-6) are then selected for screening in the in vivo the MCAO rat model (see below).

For example, candidate bone marrow cell populations can be selected for further screening if they decrease the incidence of OGD-induced cell death by more than about 25% and increase the amount of secreted trophic factors by at least 10% or more.

In Vivo Screening of Candidate Bone Marrow Cell Populations Capable of Treating Neurodegeneration Candidate bone marrow cell populations, selected in the OGD assay screening step described above, are tested for their ability to treat neurodegeneration in vivo. For example, the candidate bone marrow cell populations can be tested for their ability to treat neurodegeneration in an experimental animal model of neurodegeneration including transgenic models of neurodegenerative diseases (see, for example, Harvey et al. Transgenic animal models of neurodegeneration based on human genetic studies J Neural Transm. (2011) 118(1): 27-45; Trancikova et al. Genetic mouse models of neurodegenerative diseases. Prog Mol Biol Transl Sci. (2011); 100:419-82; Chan et al. Generation of transgenic monkeys with human inherited genetic disease Methods (2009) 49(1):78-84; Rockenstein et al. Transgenic animal models of neurodegenerative diseases and their application to treatment development Adv Drug Deliv Rev. (2007) 59(11):1093-102).

In one embodiment, the experimental animal model of neurodegeneration can be an animal model of stroke/cerebral ischemia (review by Graham et al. Comp Med. 2004 54(5):486-96), such as the MCAO rat model, where constriction of a surgically implanted ligature around a cerebral artery mimics the effect of ischemic stroke by limiting the blood flow to the brain and causes ischemia and subsequent neurodegeneration.

In the transient MCAO model, a candidate bone marrow cell population, selected in the OGD assay, is administered by constant rate infusion into the blood stream of a transient MCAO rat. One or ordinary skill in the art can determine suitable dosages that can range, for example, from $7.5 \times 10^4$ to $3.75 \times 10^7$ cells. The cells can be injected into, for example, either the jugular vein (IV) or the carotid artery (ICA). Controls consist of administration of an equivalent volume of cryopreservation media or saline solution. Cells within the candidate bone marrow population then migrate to the site of the infarct caused by the transient MCAO.

Neurologic function in the presence or absence of the OGD selected bone marrow cell populations is then evaluated using a modified Bederson Neurologic Test at various times post-infarction. The rats are then sacrificed and the volume of infarction and host cell survival are measured by hematoxylin and eosin (H&E) or Nissl staining of brain tissue sections from treated and untreated MCAO rats. Bone marrow cell populations are then selected according to their ability to improve neurologic function, increase host cell survival and decrease the volume of infarction as compared to control animals up to 28 days post-MCAO.

Combination Therapies for the Treatment of Neurodegeneration Caused by Ischemic Stroke Stopping blood flow through the middle cerebral artery for an extended period of time simulates permanent arterial occlusion with a blood clot. Transient occlusion, where blood flow through the cerebral artery is stopped for a limited period of time before being restored to allow reperfusion is intended to mimic therapies such as thrombolysis or mechanical clot removal that restore blood flow to the stroke penumbra immediately after arterial blockage caused by ischemic stroke.

In many respects, the administration of the NCS-01 cell population to transient MCAO rats simulates reperfusion of occluded arteries as a result of thrombolysis or mechanical removal of blood clots including angioplasty or surgical implantation of stents.

When neurodegeneration is cause by ischemic stroke, NCS-01 cell population can be combined with thrombolytic therapies for the treatment of neurodegeneration caused by ischemia. A description of thrombolytic agents and their administration can be found, for example, in U.S. Pat. Nos. 5,945,432 and 6,821,985.

Thrombolytic agents injected after an ischemic event can be administered either before, together or after the injection of the NCS-01 cell population.

Non-limiting examples of mechanical procedures to improve blood flow to a stroke penumbra that may be used in conjunction with the injection of the disclosed NCS-01 cell composition include angioplasty or the implantation of stents according to procedures that are well known in the art.

The present invention will be described in further detail with reference to the following examples.

EXAMPLES

The examples set forth methods for isolating, selecting and using subpopulations of bone marrow cells for treating neurodegeneration according to the present invention. It is understood that the steps of the methods described in these examples are not intended to be limiting. Further objectives and advantages of the present invention other than those set forth above will become apparent from the examples which are not intended to limit the scope of the present invention.

Example 1: Isolation of the NCS-01 Cell Population

1) Isolation of Candidate Bone Marrow Cell Populations

A heterogeneous bone marrow cell population was isolated by the following manufacturing process:

Human unprocessed bone marrow was harvested from pre-screened healthy donors of 50 years of age or younger by qualified commercial vendor. The bone marrow was harvested from a donor that was not pretreated with any anti-mitotic agent such 5-fluorouracil.

The bone marrow, whether processed or unprocessed, was then seeded at low density ($10^2$-$10^6$ cells/cm$^2$) onto a tissue/cell culture plastic surface and cultured in the presence of serum-containing media;

after a few days to allow for cell adherence to the plastic, non-adherent cells were removed by washing; and culturing the adherent cell population to near confluence in serum-containing media; serially passaging the population of cultured cells for no more than about 7 serial passages, wherein, at each passage, the cultured cells are seeded at a low density.

To select the optimal culture conditions for the isolation of a bone marrow cell population that can treat neurodegeneration, cell populations were initially grown under different culture conditions such as cell density at seeding, cell passage number, culture media composition or cell fractionation (see Table I).

Bone marrow cells from unprocessed bone marrow or after density fractionation or ACK lysis were seeded on to tissue/cell culture plastic in presence of α-MEM supplemented with 2 mM GlutaMax (Invitrogen) and 10% fetal bovine serum (FBS, HyClone or GIBCO) or α-MEM (Mediatech) with 2 mM GlutaMax (Invitrogen) and 10% fetal bovine serum (FBS, HyClone or GIBCO) or serum free media (StemPro). After washing to remove non-adherent cells, adherent cells were allowed to proliferate to near confluence. The cells were then serially passaged for a total of 3, 4, 5 or 6 passages.

Candidate bone marrow cell populations were then tested for their ability to treat neurodegeneration in the in vitro OGD assay and in vivo MCAO study.

TABLE I

| CELLS | CELL FRACTION | CULTURE MEDIA | PASSAGES |
|---|---|---|---|
| Cell 1 | Unprocessed BM* | αMEM + 10% FBS | 3 |
| Cell 2 | Using Ficoll | αMEM + 10% FBS | 3 |
| Cell 3 | Using ACK lysis | αMEM + 10% FBS | 3 |
| Cell 4 | Using Ficoll | Serum free media (StemPro) | 6 |
| Cell 5 | Using ACK lysis | Serum free media (StemPro) | 5 |
| Cell 6 | Using Ficoll | Serum free media (StemPro) | 4 |
| Cell 7 | Using ACK lysis | Serum free media (StemPro) | 4 |

*Bone marrow

2) Primary Screening Using the In Vitro Oxygen/Glucose Deprivation (OGD) Protocol Different parameters in the manufacturing process outlined above, such as bone marrow preparation in the presence or absence of density fractionation, seeding density, number of passages, culture media and/or their combination were evaluated using the in vitro oxygen/glucose deprivation (OGD) experimental protocol to determine the optimal procedure for the isolation of a candidate bone marrow cell population that can treat neurodegeneration.

The in vitro OGD model was chosen as an initial screen because it mimics neurodegeneration caused by ischemic stroke. Specifically, OGD tested whether or not a specific candidate bone marrow cell subpopulation can prevent neural cell death in culture and induce the secretion of neuroprotective trophic factors, such as bFGF and IL-6.

In the in vitro oxygen glucose deprivation (OGD) model, primary mixed cultures of rat neurons and astrocytes (at a 1:1 ratio) were exposed to OGD injury (8% oxygen; glucose-free Earle's balanced salt solution) for 90 minutes and returned to physiological conditions for 2 hours, after which, a candidate bone marrow cell populations was added to the OGD treated neuron-astrocyte co-culture for an additional 3 more hours. Neural cell viability was evaluated immediately after OGD and at 5 hours after OGD using standard trypan blue staining and MTT (3-(4,5-Dimethylthiazol-2-yl)-2,5-diphenyltetrazolium bromide) methodologies.

Cell Culture

Primary mixed cultures of rat neurons and astrocytes were maintained in culture following the supplier's protocol (CAMBREX, MD) Immediately after thawing, cells ($4 \times 10^4$ cells/well) were seeded and grown in 96-well plates coated with poly-lysine in Neuro basal media (GIBCO, CA) containing 2 mM L-glutamine, 2% B27 (GIBCO, CA) and 50 U/ml penicillin and streptomycin for 7-10 days at 37° C. in humidified atmosphere containing 5% $CO_2$. The purity of the neuronal and astrocytic cell populations was then evaluated using MAP2 and GFAP immunostaining, respectively, and found to be greater than 99%.

Oxygen-Glucose Deprivation (OGD) and Co-Culture with Candidate Bone Marrow Cell Populations Cultured cells were exposed to the OGD injury model as described previously (Malagelada et al., Stroke (2004) 35(10):2396-2401) with few modifications. Briefly, culture medium was replaced by a glucose-free Earle's balanced salt solution (BSS) having the following composition: 116 mM NaCl, 5.4 mM KCl, 0.8 mM $MgSO_4$, 1 mM $NaH_2PO_4$, 26.2 mM $NaHCO_3$, 0.01 mM glycine, 1.8 mM $CaCl_2$, and the pH was adjusted to 7.4. Cultured cells were placed in a humidified chamber to equilibrate with a continuous flow of 92% $N_2$ and 8% $O_2$ gas for 15 minutes. After equilibrium was achieved, the chamber was sealed and placed in an incubator at 37° C. for 90 minutes. After this time period, OGD was ended by adding glucose to the culture medium and returning the cultures to the standard 95% $O_2$ and 5% $CO_2$ incubator. A 2-hour period of 'reperfusion' in standard medium and normoxic conditions were then allowed, after which, a candidate bone marrow (BM) cell population was added to the OGD-treated mixed neuronal-glial culture for about 3 hours. The supernatant and the bone marrow cell population were then separated from the mixed culture by washing. Thereafter, cell viability and immunocytochemistry were performed on the cells and the amounts of secreted trophic factors were measured using commercially available ELISA assays as described below.

Cell Viability Assays

Cell viability was evaluated at two time points: immediately after OGD and 5 hours after OGD (i.e., 2 hours of reperfusion plus 3 hours of treatment with the selected bone marrow cell population). For the post-OGD viability assay, the supernatant containing the bone marrow derived cells was separated from the adherent mixed neural cell culture. Trypan blue staining method was conducted and mean viable cell counts were calculated in three randomly selected areas (0.2 $mm^2$) in each well (n=5 per treatment condition) to reveal the cell viability for each treatment condition. In addition, Trypan blue staining was performed on subsets of bone marrow derived cells harvested as pellets from the supernatant.

ELISA Assays

Trophic factors such as bFGF and IL-6 as well as possible neurotrophic factors secreted by bone marrow-derived cells presumably participate in the treatment of neurodegeneration simulated by the OGD culture conditions. Thus, measuring the amount of these molecules secreted into the culture media provides criteria by which to evaluate candidate bone marrow cell populations that can treat neurodegeneration in vivo. Supernatants from co-cultures of neural cells and candidate bone marrow cell populations under standard culture conditions or exposed to OGD were collected and analyzed for the presence of trophic factor secretion using commercially available ELISA kits in accordance with the manufacturer's instructions.

Figure 1B:
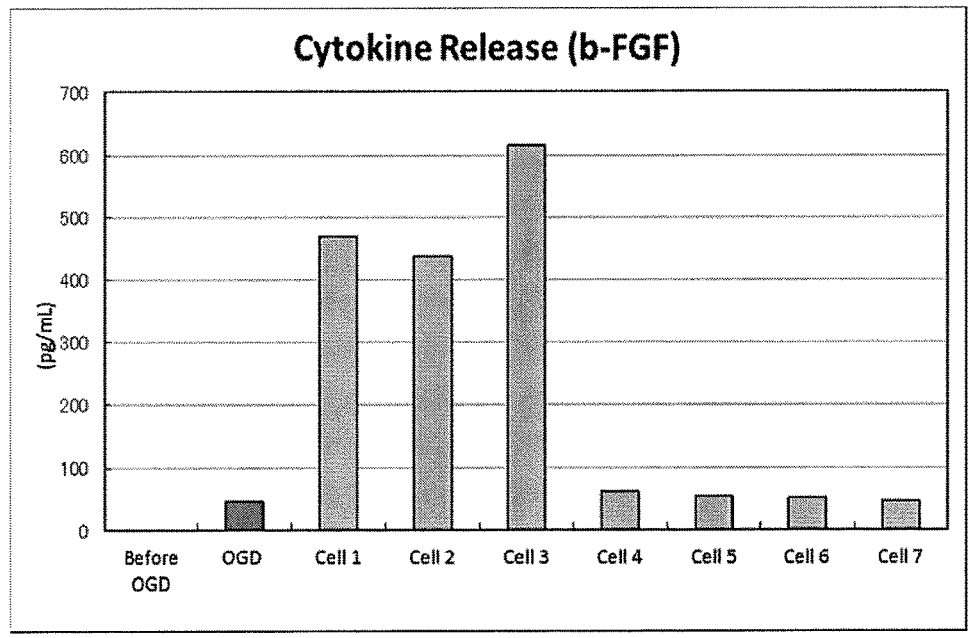
Figure 1B:
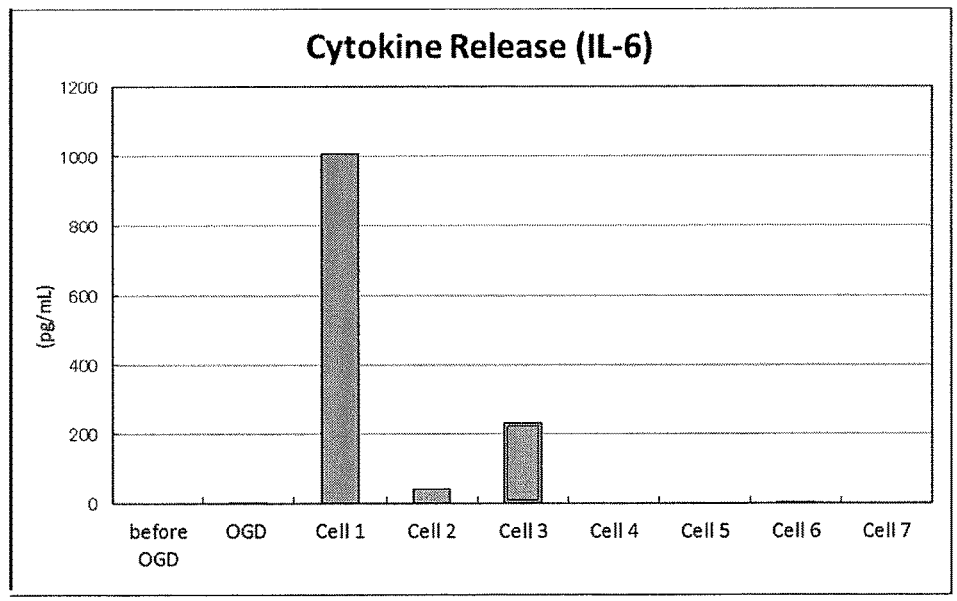

The results of an OGD analysis of the bone marrow derived cell populations processed according to the parameters depicted in Table I above, are shown in FIGS. 1A and 1B.

Based on the results depicted in FIGS. 1A and 1B, αMEM+10% FBS was chosen as the optimal cell culture medium and unprocessed bone marrow was found to be superior to bone marrow processed by density fractionation (such as Ficoll-Paque or Percoll) or by ACK lysis. The optimal passage number for unprocessed bone marrow cells in αMEM+10% FBS medium was found to be no more than 7 passages.

3) Secondary Screening and Selection of Candidate Bone Marrow Cell Populations Using the In Vivo Middle Cerebral Artery Occlusion Rat Model Based on the results obtained with the initial screening in the in vitro OGD model, the biological activity of each candidate bone marrow cell population to treat neurodegeneration was evaluated by comparing the neurological deficit and the volume of infarction of MCAO rats treated with the candidate bone marrow cell population with MCAO rats treated receiving only saline solution.

Middle Cerebral Artery Occlusion (MCAO) Surgery

Animals were anesthetized using isoflurane (1.5%-2.5% with oxygen). The scalp skin was shaved and scrubbed with alcohol and chlorhexidine surgical scrub. The animal was then placed in a stereotaxic apparatus. Starting slightly behind the eyes, a midline sagittal incision about 2.5 cm long was made, and the skull area was exposed using the rounded end of a spatula. With the bregma as a reference point, baseline (i.e., prior to stroke surgery) laser Doppler recording was obtained from the following coordinates (AP: +2.0, ML: ±2.0). The skin on the ventral neck was shaved from the jaw to the manubrium and scrubbed with alcohol and chlorhexidine surgical scrub. The animal was then moved under the surgical microscope. A skin incision was made over the right carotid artery. The external carotid was isolated and ligated as far distally as possible. The occipital artery was cauterized. Occasionally there was another branch or two extending from the external carotid that may also need to be cauterized. A second ligature was placed proximally on the external carotid artery, which was then cut between the ligatures. The pterygopalatine artery was ligated. Following this, a temporary suture was placed around the common carotid to provide tension and restrict blood flow. The proximal stump of the external carotid was pulled back using the ligature, effectively straightening the carotid bifurcation. An incision using a pair of microscissors was made in the stump of the external carotid and a 4-0 nylon filament with a pre-fabricated end was inserted and passed up into the internal carotid until resistance was felt (approximately 15-17 mm) This effectively blocks the middle cerebral artery (MCA). The filament was secured in place with a ligature around the proximal stump of the external carotid. The contralateral common carotid was isolated and secured with a temporary ligature. The skin incision was closed with staples. The animal was then fixed to the stereotaxic apparatus for laser Doppler recording to reveal successful MCA occlusion. After five minutes, the ligature to the contralateral common carotid artery was removed. The isoflurane was discontinued and the animal was placed in a recovery cage over a warming blanket. After 60 minutes, the animal was anesthetized again with isoflurane and the incision was opened for testing in the transient model. The filament causing the occlusion was removed and the stump of the external carotid ligated close to the carotid bifurcation. The skin incision was closed with staples. The animal was again fixed to the stereotaxic apparatus for laser Doppler recording to reveal successful reperfusion. Finally, the animal was placed in a recovery cage over a warming blanket.

Neurological Function Tests

The well-recognized modified Bederson Neurologic Test was performed for each rat and involves obtaining a score from each of the following:

contralateral hind limb retraction, which measures the ability of the animal to replace the hind limb after it was displaced laterally by 2-3 cm, graded from 0 (immediate replacement) to 3 (no replacement), beam walking ability, graded 0 for a rat that readily traverses a 2.4-cm-wide, 80-cm-long beam to 3 for a rat unable to stay on the beam for 10 seconds, and bilateral forepaw grasp, which measures the ability to hold onto a 2-mm-diameter steel rod, graded 0 for a rat with normal forepaw grasping behavior to 3 for a rat unable to grasp with the forepaws.

The scores from all 3 tests were assessed over a period of about 15 minutes on each assessment day. An average score was calculated from the 3 tests to provide a composite neurologic deficit score that ranges from 0 (normal neurological function) to a maximum of 3 (severe neurological deficit). Thus, the higher the score, the greater the neurological deficit.

Based on pilot studies, a score above about 2.5 indicates an animal has neurological deficits characteristic of stroke.

Histology

Brain Section Preparation

Brain section preparation is designed to identify regions of cerebral injury. At 7 days or 28 days after MCA occlusion, rats were euthanized, perfused by trans-cardiac perfusion with saline, followed by 4% paraformaldehyde. The brains were then fixed in 4% paraformaldehyde, and subsequently immersed in 25% sucrose. Each forebrain was cut into 30 μm thick coronal tissue sections with anterior-posterior coordinates corresponding from bregma 5.2 mm to bregma −8.8 mm per animal.

Measurements of Infarction Volume

At least 4 coronal tissue sections per brain were processed for hematoxylin and eosin (H&E) or Nissl staining. The indirect lesion area, in which the intact area of the ipsilateral hemisphere was subtracted from the area of the contralateral hemisphere was used to reveal cerebral infarction.

The lesion volume was presented as a volume percentage of the lesion compared to the contralateral hemisphere. Histological determination of the lesion volume was performed using hematoxylin and eosin (H&E) or Nissl staining, with representative images captured digitally and processed via NIH Image J software, and quantitative image analysis. The lesion volume was determined according to the following formula:

Thickness of the section×sum of the infarction area in all brain sections.

To minimize artifacts produced by post-ischemic edema in the infarcted area, the infarction area in the ipsilateral hemisphere was indirectly measured by subtracting the non-infarction area in the ipsilateral hemisphere from the total intact area of the contralateral hemisphere.

Measurements of Cell Survival in Ischemic Peri-Infarct Area

A randomly selected high power field corresponding to the cortical peri-infarct area was used to count cells surviving in this ischemic region (Yasuhara et al., Stem Cells and Dev, 2009). For an estimation of host neuronal cell viability within the ischemic cortical region, Nissl staining was performed using Crystal violet solution (Sigma, St. Louis, Mo.), and randomly selected visual fields of the cortical region and corresponding contralateral intact cortex in 3 sections were captured photographically (Carl Zeiss, Axiophot2), and cell numbers were determined by counting cells in randomly selected high power field views (28,800 µm2) The percentages of preserved neurons in damaged cortex relative to the intact side were calculated and used for statistical analyses. Brain sections were blind-coded and the total number of counted stained cells was corrected using the Abercrombie formula.

Screening of Candidate Bone Marrow Cell Populations Using the MCAO Stroke Animal Model Groups of 3 (for IV administration) or 6 (for ICA administration) male rats/group were subjected to 1 hr. transient MCAO and then injected with 1 ml of injection medium containing either saline or $7.5 \times 10^6$ bone marrow-derived cells (called NCS-01 cell population) isolated according to the protocol described above Animals were followed for up to 7 days post cell administration.

Figure 1C:
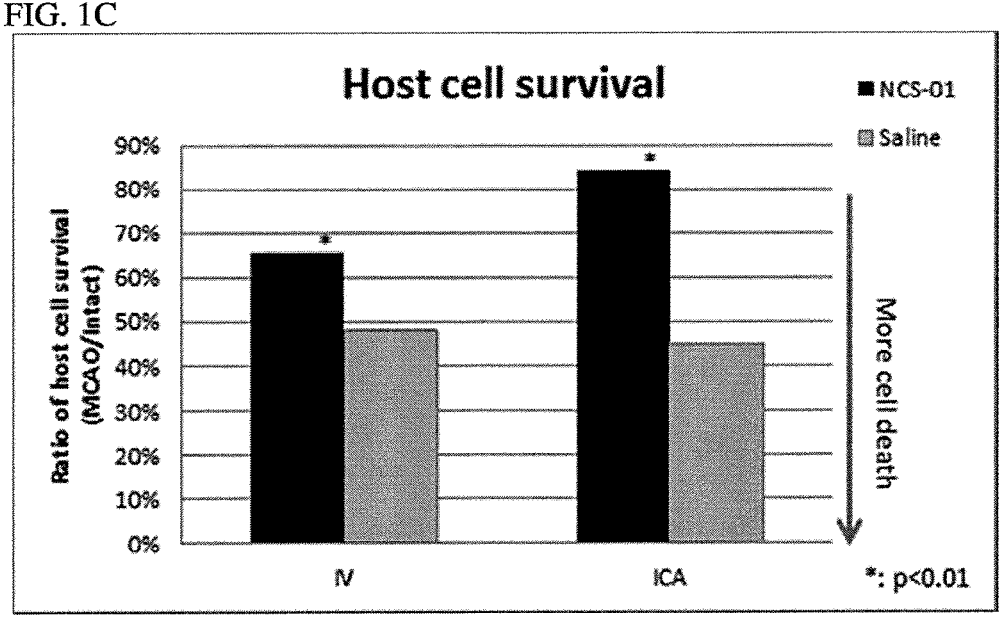
FIGS. 1C and 1D compares host cell survival, infarction volume and neurological function in the in vivo MCAO rat model in response to the NCS-01 bone marrow cell sub-population or saline injected either intravenously (IV) or intra-arterially (ICA).
Figure 1D:
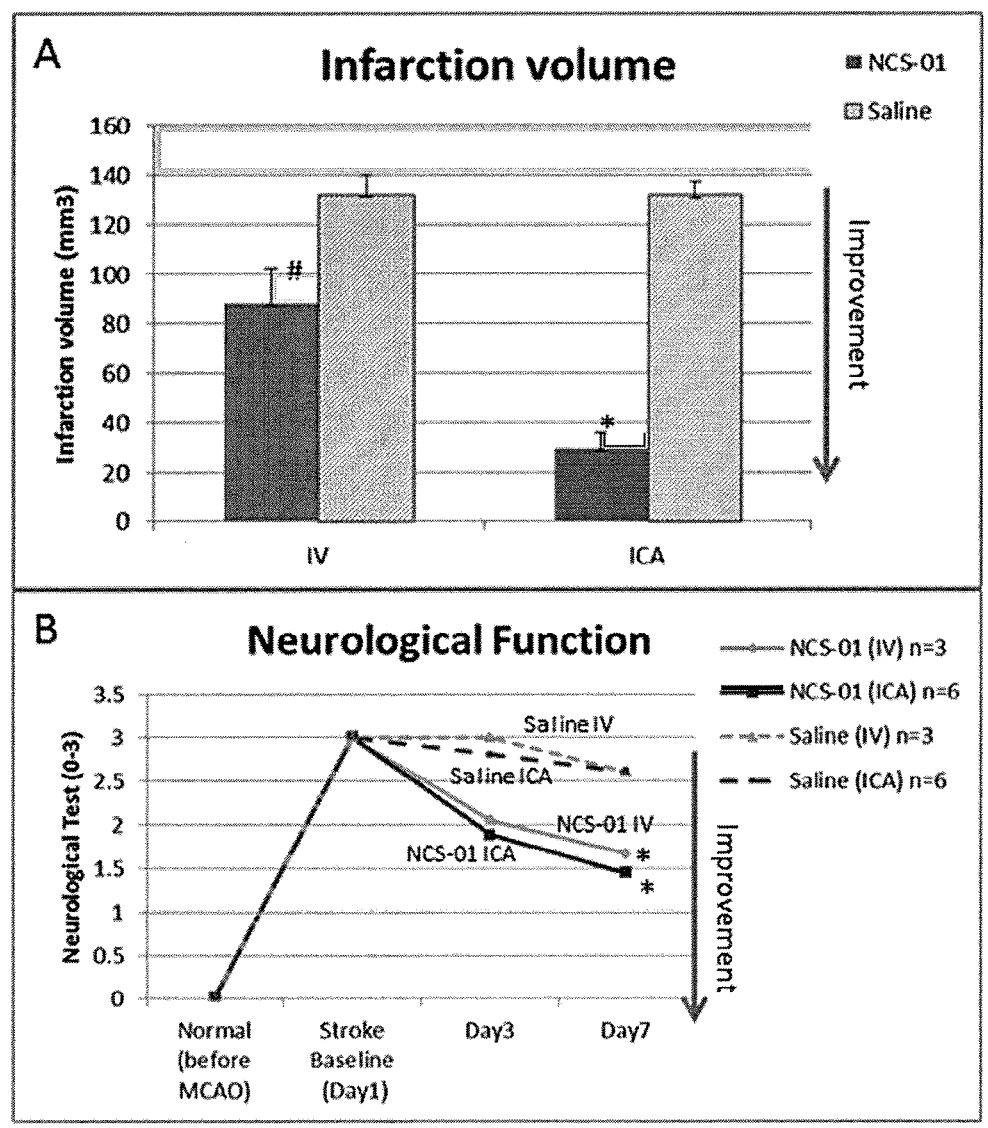

FIGS. 1C and 1D shows that IV or ICA-administered NCS-01 bone marrow cell population provided substantial neurologic and pathologic benefit, when administered in rats with transient MCAO. Moreover, NCS-01 prevented host cell death by treating ischemia-induced neurodegeneration with consequent reduction in infarction volume and improvement of neurological deficit.

The primary in vitro and secondary in vivo screening procedures were repeated until the process reliably and reproducibly produced an optimal subpopulation of bone marrow derived cells (called NCS-01 cell population) that was able to treat neurodegeneration.

Figure 1E:
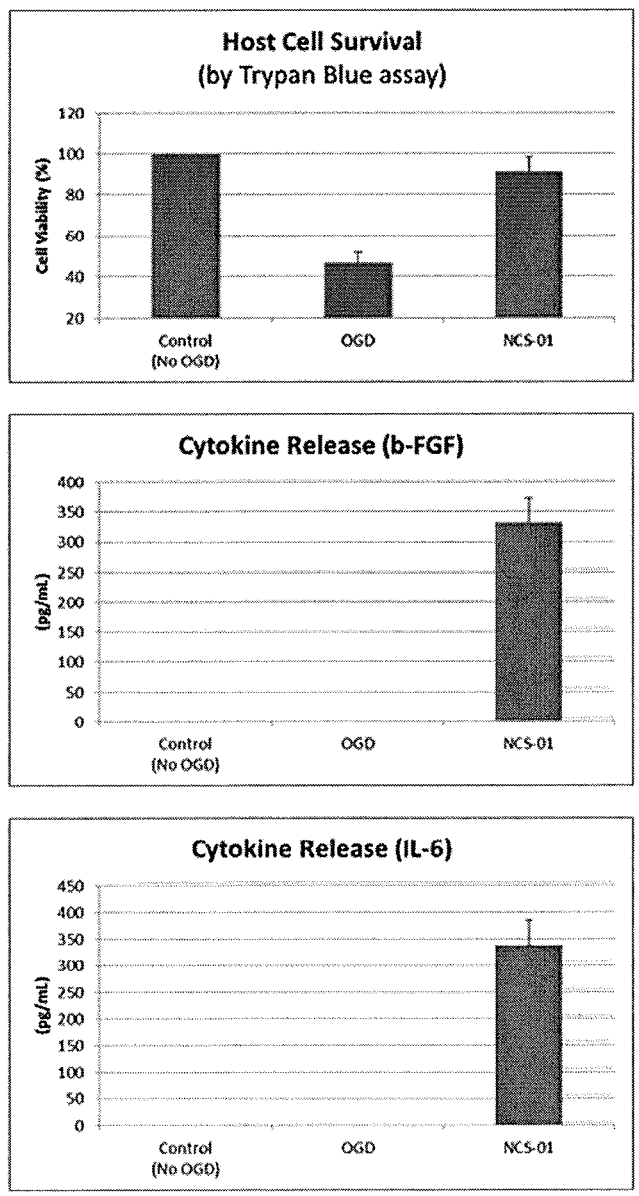
FIG. 1E depicts host cell survival and cytokine release (bFGF and IL-6) in the in vitro OGD model in response to the presence or absence of the NCS-01 bone marrow cell subpopulation.
Figure 1F:
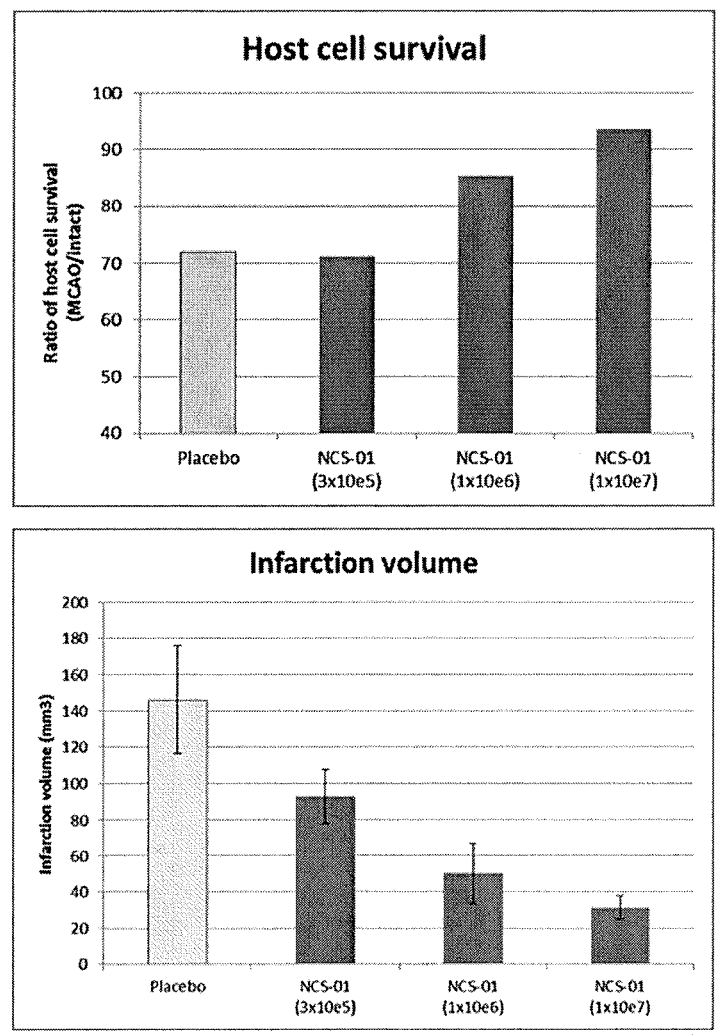
FIG. 1F shows changes in infarction volume and neurological function in the in vivo MCAO rat model in response to the injection of $3 \times 10^5$, $10^6$ and $10^7$ NCS-01 bone marrow cells.

The optimized NCS-01 cell population was again tested in the in vitro OGD model to confirm anti-neurodegeneration activity in a co-culture of human neurons and astrocytes (see FIG. 1E) and in the in vivo rat MCAO model (FIG. 1F). The experiment depicted in FIG. 1F also shows the ability of NCS-01 cell population to treat neurodegeneration is dose dependent.

Example 2: Standardized Manufacturing Procedure for the Product of the NCS-01 Cell Population that is Able to Treat Neurodegeneration Whole, unprocessed bone marrow is harvested from a mammal that is not pre-treated with any anti-mitotic or anti-metaolite agent, such as 5-fluorouracil (5-FU). Because the bone marrow is not processed by density fractionation or ACK lysis, the starting whole bone marrow cell population can include hematopoietic and non-hematopoietic cells as well as both nucleated and non-nucleated bone marrow cells.

The above unprocessed bone marrow is diluted and seeded at low density (105-106 cells/cm2) onto a tissue/cell culture plastic surface and cultured in the presence of serum-containing media (α-MEM (phenol red free) supplemented with 2 mM GlutaMax (Invitrogen) and 10% fetal bovine serum (FBS, HyClone or GIBCO) or α-MEM (Mediatech) with 2 mM GlutaMax (Invitrogen) and 10% fetal bovine serum (FBS, HyClone or GIBCO)). The cell cultures are then incubated at 37° C., 5% $CO_2$, 80% RH (relative humidity) for 72 hours;

The cells are rinsed with D-PBS to remove non-adherent cells and RBCs from the cell culture plastic followed by a complete medium exchange with supplemented α-MEM, which is used for all subsequent feedings. Cell cultures (at passage 0 or p0) were then incubated at 37° C., 5% CO2, 80% RH.

For passage 1, the cells are rinsed with D-PBS and the plastic adherent cells are detached using a cell dissociation reagent. Dissociated cells are harvested by centrifugation at 300 g (~1000 rpm) for 8-10 minutes. The pelleted cells are re-suspended with supplemented α-MEM and seeded at a density of approximately 750 cells/cm$^2$ onto a tissue/cell culture plastic surface.

The cells are cultured to near confluence before additional passaging.

Cells are harvested and again seeded again at a density of approximately 750 cells/cm$^2$ onto a tissue/cell culture plastic surface as described above for passage 2.

For passage 3, cells are harvested using a cell dissociation reagent and centrifuged as described above. The pelleted cells are then resuspended and pooled. Cells are resuspended in a cryopreservation media and 1 mL cell suspension aliquoted into Cryovials (Nunc). Vials are frozen using a control-rate freezer and once the freezing program is complete, transferred on dry ice for permanent storage in a vapor-phase Liquid Nitrogen freezer.

The vials containing cells at passage 3 (p3) constitute the MCB.

One vial of MCB is thawed and the recovered cells (passage 4 or P4) are seeded on to tissue/cell culture plastic at a density of approximately 750 cells/cm$^2$ in α-MEM supplemented with 10% FBS and GlutaMAX™. The cells are then incubated at 37° C., 5% $CO_2$, 80% RH.

For passage 4, the cells are cultured to near confluence before additional passaging. Cells are harvested and seeded onto new tissue/cell culture plastic surface as described above.

For passage 5, cells are harvested and frozen, following the methods described above for the MCB. Cells that are aliquoted into vials and cryopreserved at passage 5 (P5) constitute the WCB.

When needed, one vial of WCB is thawed and the recovered cells are seeded on to tissue/cell culture plastic at a density of approximately 750 cells/cm$^2$ in α-MEM supplemented with 10% FBS and GlutaMAX™. The cells are then incubated at 37° C., 5% $CO_2$, 80% RH.

For passage 6, the cells are cultured to near confluence before additional passaging. Cells are harvested and seeded onto new tissue/cell culture plastic surface as described above.

Culture media is changed in the middle of passage (WCB to passage 6 and passage 6 and passage 7).

For passage 7, cells are harvested and frozen, following the methods described above for the MCB.

Example 3: Treatment of Neurodegeneration Caused by Permanent Versus Transient Middle Cerebral Artery Occlusion (MCAO) with NCS-01 Cells The infarction volume and neurologic function of NCS-01 treated rats with permanent MCAO was compared to that of NCS-01 treated rats with transient (60 minutes) MCAO.

The transient MCAO simulates the treatment of arterial occlusion caused by stroke with now standard clinical procedures that restore blood flow to the stroke penumbra. These procedures include the administration of thrombolytic drugs as well as procedures such as angioplasty and/or vascular stenting that involve the mechanical removal of blood clots.

Groups of 3 or 6 rats were subjected to either permanent or transient MCAO (with reperfusion). Either saline or $7.5 \times 10^6$ NCS-01 cells in 1 ml were then administered ICA 24 hours post-ischemia and rats were monitored for up to 28 days. Neurologic function was then evaluated using the modified Bederson Neurologic Test. The transient occlusion model mimics the situation in which a stroke patient was treated with tPA, or was subjected to clot removal.

Figure 2:
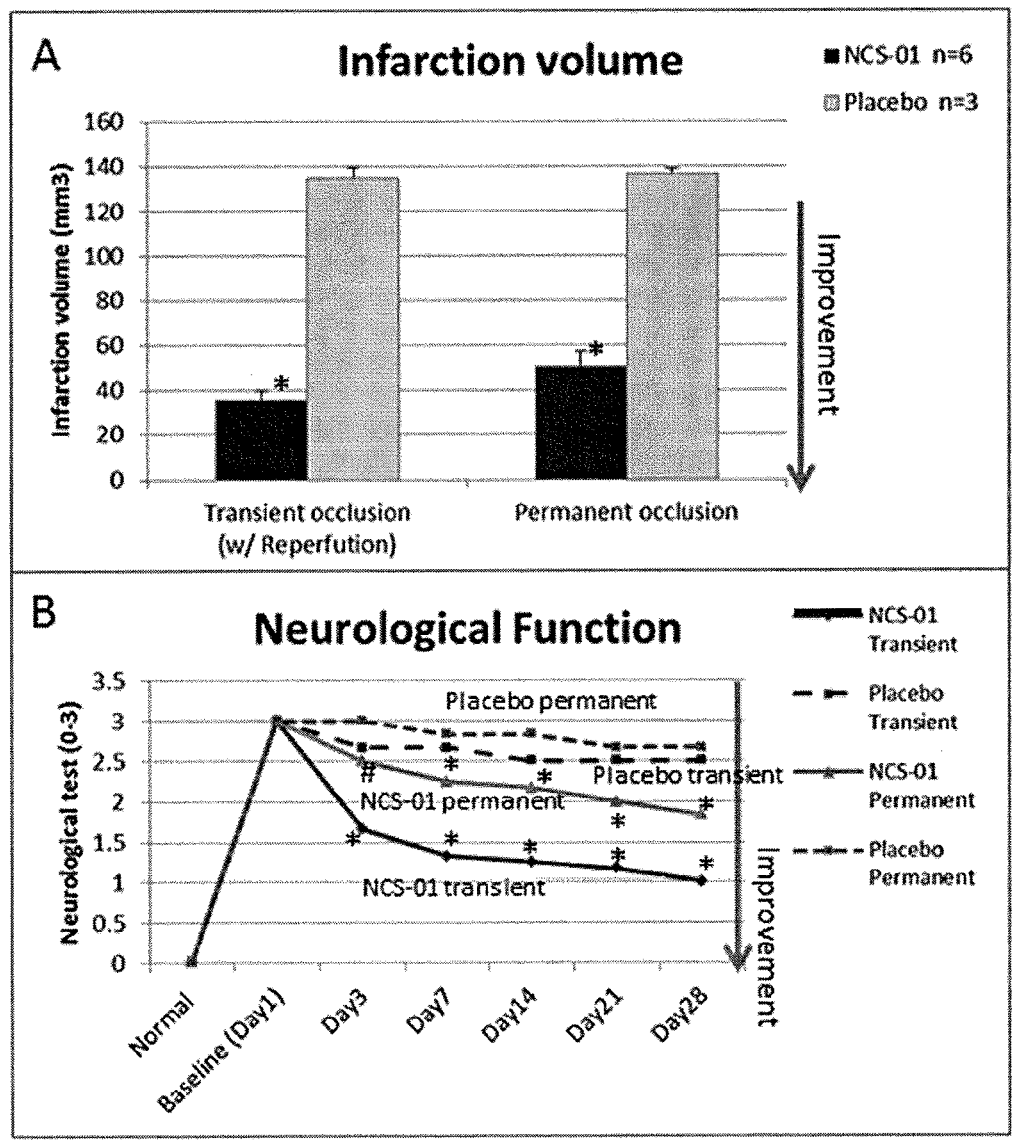
FIG. 2 shows changes in infarction volume (Panel A) and neurological function (Panel B; as measured by the Modified Bederson Scale (0=normal to 3=most severe)) in a transient (60 minutes) or permanent MCAO rat model in response to the ICA injection of 1 ml of $7.5 \times 10^6$ NCS-01 cells or saline solution.

The results in FIG. 2 show significant histological (infarction volume; Panel A) and clinical (modified Bederson Scale; Panel B) benefit with NCS-01 cell population treatment in both MCAO paradigms. Benefit was 2- to 3-fold greater in the transient occlusion model than in the permanent occlusion model. The time course of the neurological response (Panel B) showed steady improvement up to 28 days post-infarction, averaging 11% over this interval for un-reperfused (permanent occlusion) and untreated controls to 67% for re-perfused (transient occlusion) and NCS-01 treated animals Unexpectedly, NCS-01 was more effective in treating symptoms in the transient occlusion model, suggesting that maximum efficacy may be obtained when NCS-01 was added in conjunction with clot removal, either after administration of a thrombolytic drug or removal of the clot using a mechanical device.

Example 4: Comparison Between NCS-01 Cells and Other Bone Marrow Derived Cells

1) Isolation of a Bone Marrow Cell Population According to Li et al.

A bone marrow cell population was prepared exactly as described in the publication by Li et al. Journal of Cerebral Blood Flow and Metabolism (2000) 20: 131 1-1319 (hereafter called the Li bone marrow population).

Primary cultured bone marrow cells were obtained from adult mice that had received the anti-metabolite drug, 5-fluorouracil (5-FU, 150 mg/kg) intra-peritoneally 2 days before harvesting (Randall and Weissman, 1997). Using a 21-gauge needle connected to a 1 mL syringe with phosphate-buffered saline (PBS, 0.5 mL), fresh complete bone marrow was harvested aseptically from tibias and femurs. Bone marrow was mechanically dissociated until a milky homogenous single-cell suspension. Red blood cells were removed from bone marrow using 0.84% $NH_4Cl$ and the number of nucleated marrow cells was determined using a cytometer. $2 \times 10^6$ nucleated cells were seeded into a tissue culture flask in Iscove's Modified Dulbecco's medium supplemented with fetal bovine serum (10%). After 3 days of incubation, cells tightly adhered to plastic and were resuspended in fresh Iscove's Modified Dulbecco's medium in new flasks and were grown for another three passages.

Figure 3:
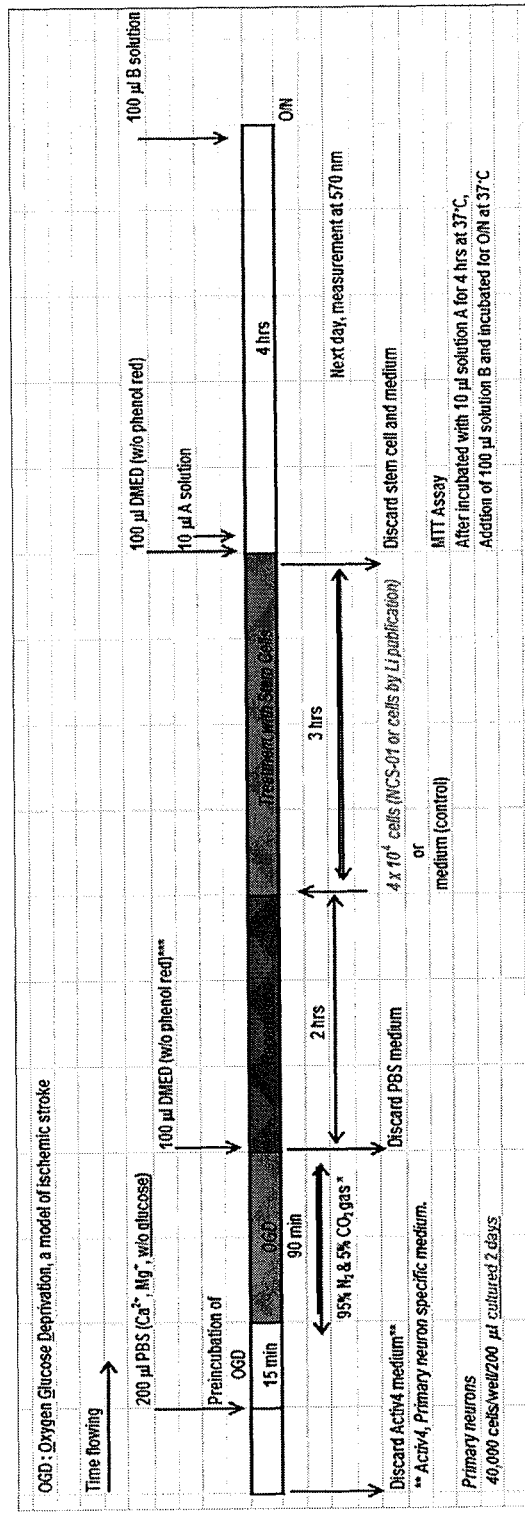
FIG. 3 depicts a schematic diagram that describes the protocol used in the in vitro Oxygen Glucose Deprivation (OGD) assay.

2) Comparison of the Li Cell Population with the NCS-01 Cell Population in the In Vitro OGD Assay Two lots of NCS-01 manufactured from different WCBs of a same MCB and bone marrow were tested together with the Li cell population in the in vitro OGD model as outlined in FIG. 3.

Figure 4:
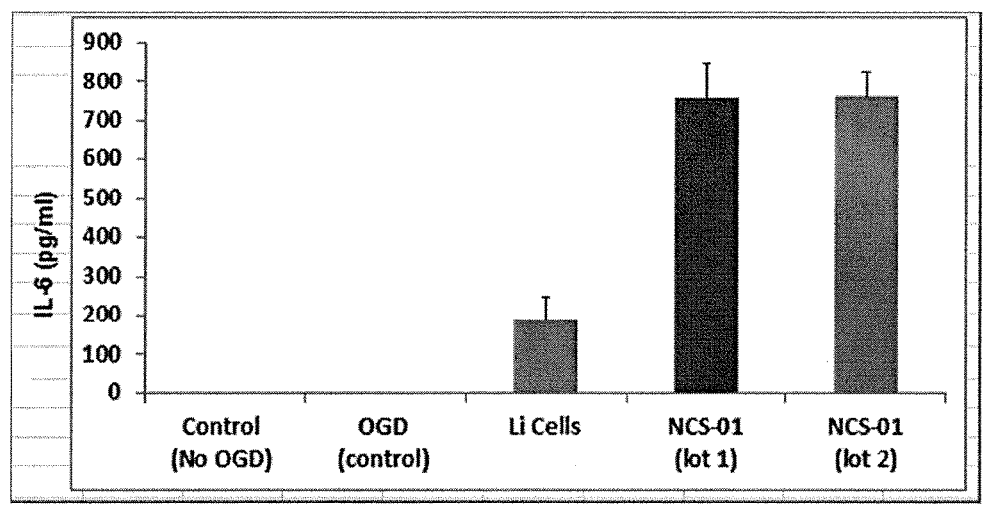
FIG. 4 shows the relative levels of secreted bFGF and IL-6 cytokines in the cell culture media of an OGD assay after addition of saline, Li cells or NCS-01 cells.
Figure 4:
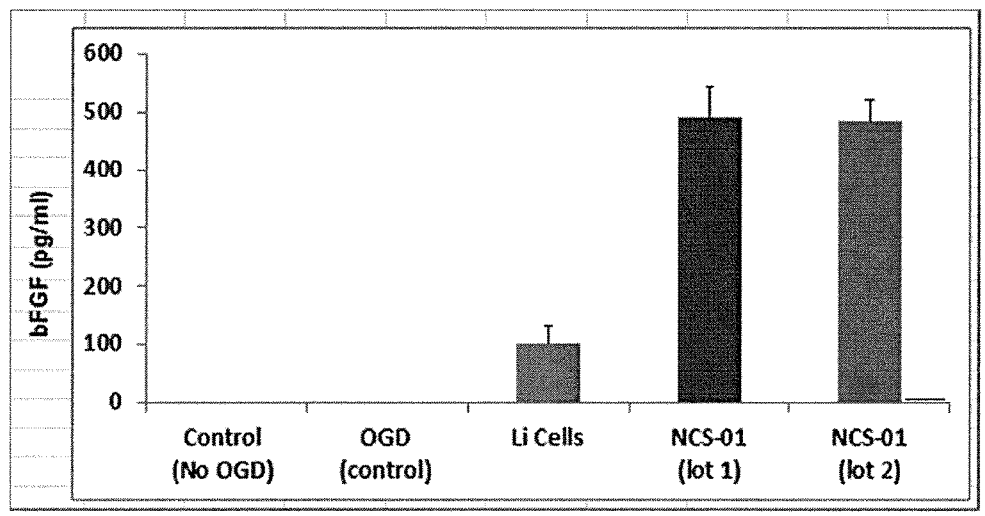

As shown in FIG. 4, both lots of NCS-01 cells generated the same increase in the secretion of both IL-6 and bFGF. Hence, NCS-01 cell populations produced by the optimized manufacturing procedure described above consistently treated neurodegeneration in the in vitro OGD assay.

In contrast, the Li cell population, that was isolated exactly as described in the Li (2000) publication, produced 4-5x less bFGF and IL-6 than NCS-01 cell population in the OGD assay.

Figure 5A:
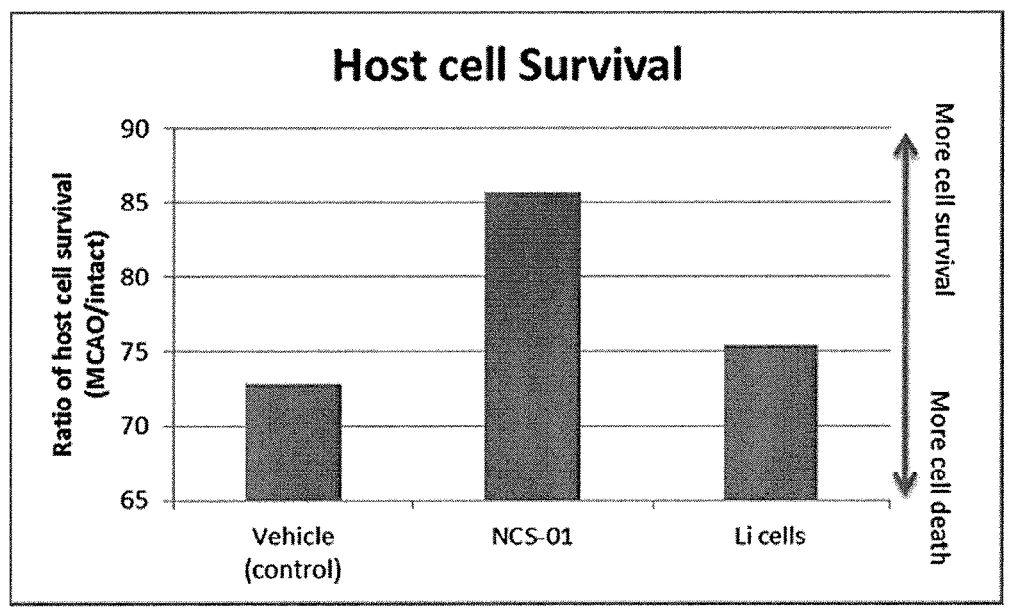
FIGS. 5A and 5B depicts host cell survival, infarction volume and neurological function in the in vivo MCAO rat model in response to an injection of saline, Li cells and NCS-01 cells.
Figure 5B:
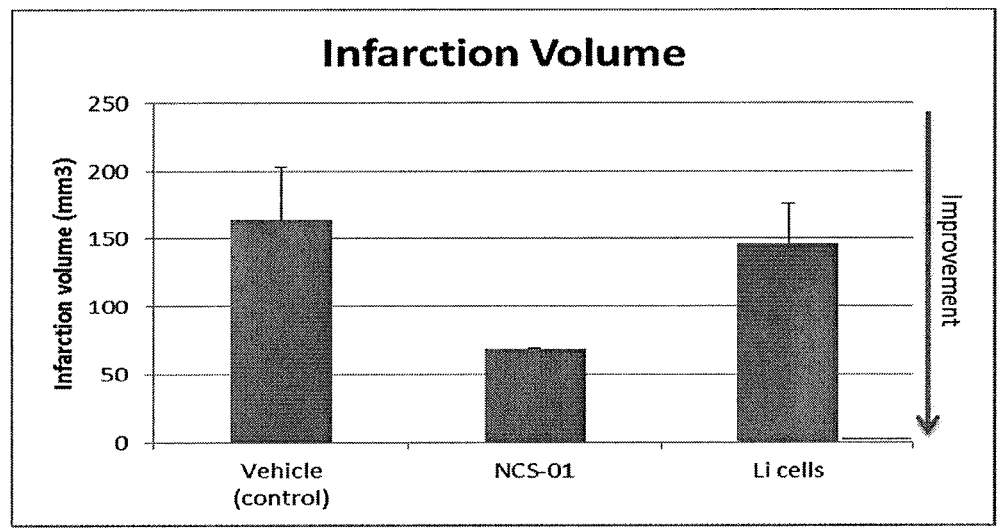
Figure 5B:
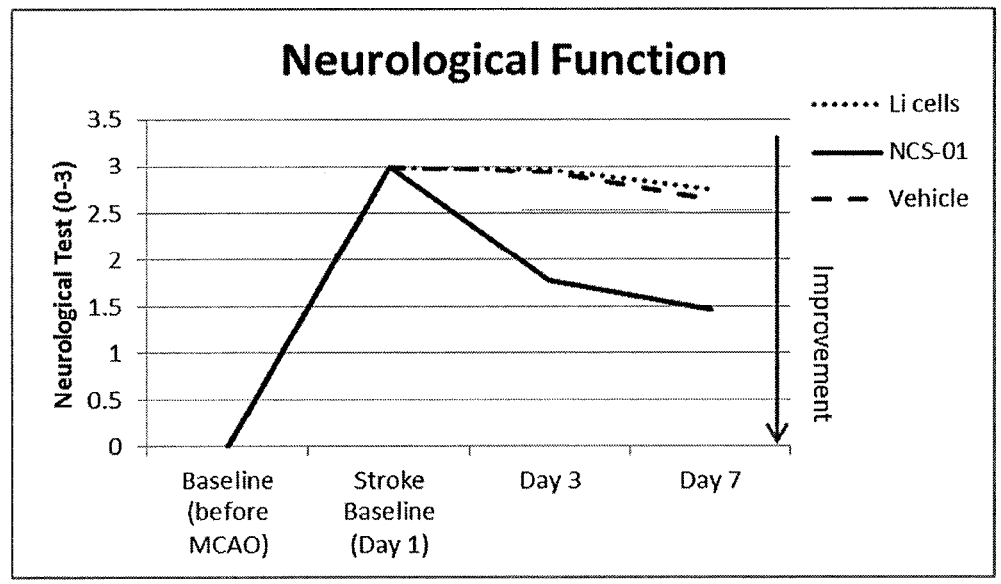

2) Comparison of the Li Cell Population with the NCS-01 Cell Population in the In Vivo MCAO Assay The ability of the NCS-01 and Li cell populations to treat neurodegeneration in vivo was tested in vivo using the MCAO rat model. The effect of the cells on host cell viability, the volume of infarction and neurological deficit are shown in FIGS. 5A and 5B. Consistent with the studies described above, the NCS-01 cell population prevented host cell death (see FIG. 5A) by treating ischemia-induced neurodegeneration with consequent reduction in infarction volume and improvement of neurological deficit (see FIG. 5B).

In contrast, the Li cell population failed to show any statistically significant activity on infarction volume or neurological function. These data therefore demonstrate that the ability of the NCS-01 population to treat neurodegeneration is defined by the manufacture process and that the NCS-01 cell population is distinct from the cell population described in the Li 2000 publication.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

The invention claimed is:

1. A method of producing a heterogeneous subpopulation of bone marrow cells for the treatment of neurodegeneration, comprising the steps in the following order:
   a) obtaining a population of bone marrow cells from unprocessed bone marrow;
   b) seeding the population of bone marrow cells at a low density onto a plastic surface,
   c) washing the seeded cell population to remove non-adherent cells;
   d) culturing the adherent cells from the washed population of cells to near confluence in serum containing media;
   e) serially passaging the cultured cells for no more than about seven serial passages, wherein, at each passage, the cultured cells are seeded at a density of about 750 cells/$cm^2$ or less at each passage in serum containing culture medium;
   f) obtaining said heterogeneous subpopulation of bone marrow cells; and
   g) testing said heterogeneous subpopulation of bone marrow cells in an experimental model of neurodegeneration which is an oxygen/glucose deprivation (OGD) cell culture model of ischemia, and selecting only those populations that demonstrate the ability to treat neurodegeneration in said model.

2. The method according to claim 1, wherein said unprocessed bone marrow is obtained from a subject that is not pre-treated with a chemotherapy agent.

3. The method according to claim 2, wherein said chemotherapy agent is 5-fluorouracil.

4. The method according to claim 2, wherein said population of bone marrow cells cannot be isolated by density fractionation or by ACK lysis.

5. The method according to claim 4, wherein said density fractionation requires a Ficoll™ or Percoll™ gradient.

6. The method according to claim 1, wherein said neurodegeneration is caused by ischemia.

* * * * *